US005700645A

United States Patent [19]
Pahuski et al.

[11] Patent Number: 5,700,645
[45] Date of Patent: Dec. 23, 1997

[54] METHODS AND KITS FOR SEPARATION, CONCENTRATION AND ANALYSIS OF CELLS

[75] Inventors: Edward E. Pahuski, Marshall; Randall L. Dimond, Madison, both of Wis.; John H. Priest, Everett, Wash.; Lisa Zandt, Madison, Wis.; Kathleen K. Stebnitz, Shorewood, Wis.; Leopoldo G. Mendoza, Madison, Wis.

[73] Assignee: Promega Corporation, Madison, Wis.

[21] Appl. No.: 485,428

[22] Filed: Jun. 7, 1995

Related U.S. Application Data

[60] Division of Ser. No. 3,242, Jan. 11, 1993, Pat. No. 5,587,286, which is a continuation-in-part of Ser. No. 547,981, Jul. 2, 1990, abandoned.

[51] Int. Cl.$^6$ .............................. C12Q 1/68; C12Q 1/66; C12N 1/00; G01N 33/44
[52] U.S. Cl. .................................. 435/6; 435/8; 435/34; 435/252.3; 435/261; 436/85; 436/177
[58] Field of Search ........................... 424/93.1, 317.1, 424/489, 524, 535, 537, 543, 545; 435/4, 8, 6, 30, 252.3, 261; 436/20, 21, 22, 23, 172, 175, 177, 178, 85

[56] References Cited

U.S. PATENT DOCUMENTS

| 4,379,849 | 4/1983 | Heimreid | 436/177 |
|---|---|---|---|
| 4,622,362 | 11/1986 | Rembaum | 525/54.1 |
| 5,258,285 | 11/1993 | Aegidius | 435/8 |

OTHER PUBLICATIONS

S.M. Charlett, "An Improved Staining Method for the Direct Microscopical Counting of Bacteria in Milk," Dairy Industry, Aug. 1954, pp. 652–653.

S.H.C. Lin, et al., "Effect of Calcium Ion on the Structure of Native Bovine Casein Micelles," Biochemistry, vol. 11, No. 10, 1972, pp. 1818–1821.

J.E. Gilchrist, et al., "Spiral Plate Method for Bacterial Determination," Applied Microbiology, Feb. 1973, pp. 244–252.

R. Bossuyt, "Usefulness of an ATP Assay Technique in Evaluating the Somatic Cell Content of Milk," Milchwissenschaft, vol. 33, No. 1, 1978, pp. 11–13.

D.P. Theron, "Effect of Temperature and Media on Adenosine Triphosphate Cell Content in *Enterobacter aerogenes*," Journal of Food Protection, vol. 46, No. 3, Mar. 1983, pp. 196–198.

The Merck Index, 10th ed. (1983), Entry No. 6424 (Nitrilotriacetic Acid).

F. O'Connor, "Rapid Test Methods of Assessing Microbiological Quality of Milk," The Australian Journal of Dairy Technology, Jun. 1984, pp. 61–65.

(List continued on next page.)

*Primary Examiner*—David Guzo
*Assistant Examiner*—William Sandals
*Attorney, Agent, or Firm*—Foley & Lardner

[57] ABSTRACT

Processes are provided for removal of cells as cell pellets from liquid milk samples, or from cultures or extracts of other food materials or other materials of biological origin. The concentrated cells in the pellet can be analyzed by various techniques to determine the relative cell count, such as by lysing of the cells followed by measurement of ATP. Nucleic amplification, as by the polymerase chain reaction method, can be carried out using the cellular pellet directly, without need for isolation of nucleic acid from the cells. After the amplification, an assay can be carried out for amplified nucleic acid segment indicative of the presence of cells of interest in the sample. The invention thus provides methods for obtaining cellular components from samples of milk, and cultures or extracts of other materials, including food materials, and for determining relative contamination of milk and such other materials by microorganisms. The invention also provides kits for carrying out its various methods.

59 Claims, 8 Drawing Sheets

OTHER PUBLICATIONS

L.C. Chaplin, "Studies on Micellar Calcium Phosphate: Composition and Apparent Solubility Product in Milk over a Wide pH Range," Journal of Dairy Research, 1984, vol. 51, pp. 251–257.

K.M. Oxley, et al., "Kinetics of Antibiotic Action Study Using ATP Bioluminescence", *Bioluminescence and Chemiluminescence*, Ed. J. Scholmarich, John Wiley & Sons, New York, 1986, pp. 495–498.

Lin, et al., "A Method for Determining β–Galactosidase Activity of Yogurt Cultures in Skim Milk", Journal of Dairy Science, vol. 72, pp. 351–359, 1989.

Güssow, et al., "Direct clone characterization from plaques and colonies by the polymerase chain reaction", Nucleic Acids Research, vol. 17, p. 4000, 1989.

Ferre, et al., "Preparation of crude cell extract suitable for amplification of RNA by the polymerase chain reaction", Nucleic Acids Research, vol. 17, p. 2141, 1989.

Sumbrook, et al., Molecular Cloning Second Edition, (Cold Spring Harbor Laboratory, Cold Spring Harbor, N.Y.), pp. 121–125 and 9.14–9.23, 1989.

Mercier, et al., "Direct PCR from whole blood without DNA extraction", Nucleic Acids Research, vol. 18, No. 19, p. 5908, 1990.

Joshi, et al., "Rapid Polymerase Chain Reaction Amplification Using Intact Bacterial Cells," Biotechniques 10, 42–44, 1991.

FIG. 2 DETECTION OF ARTIFICIALLY CONTAMINATED PASTEURIZED MILK

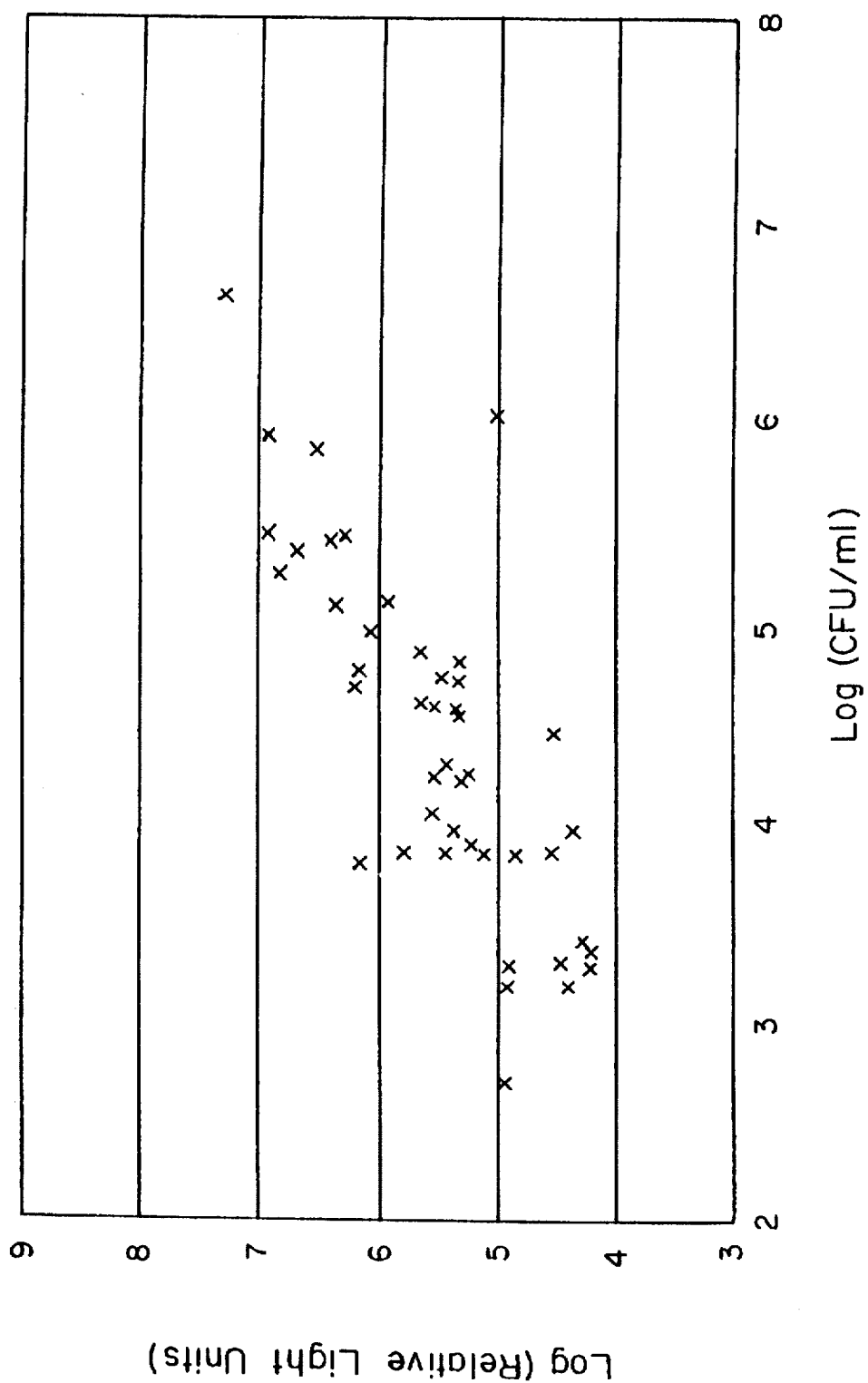
FIG. 4 Correlation Study

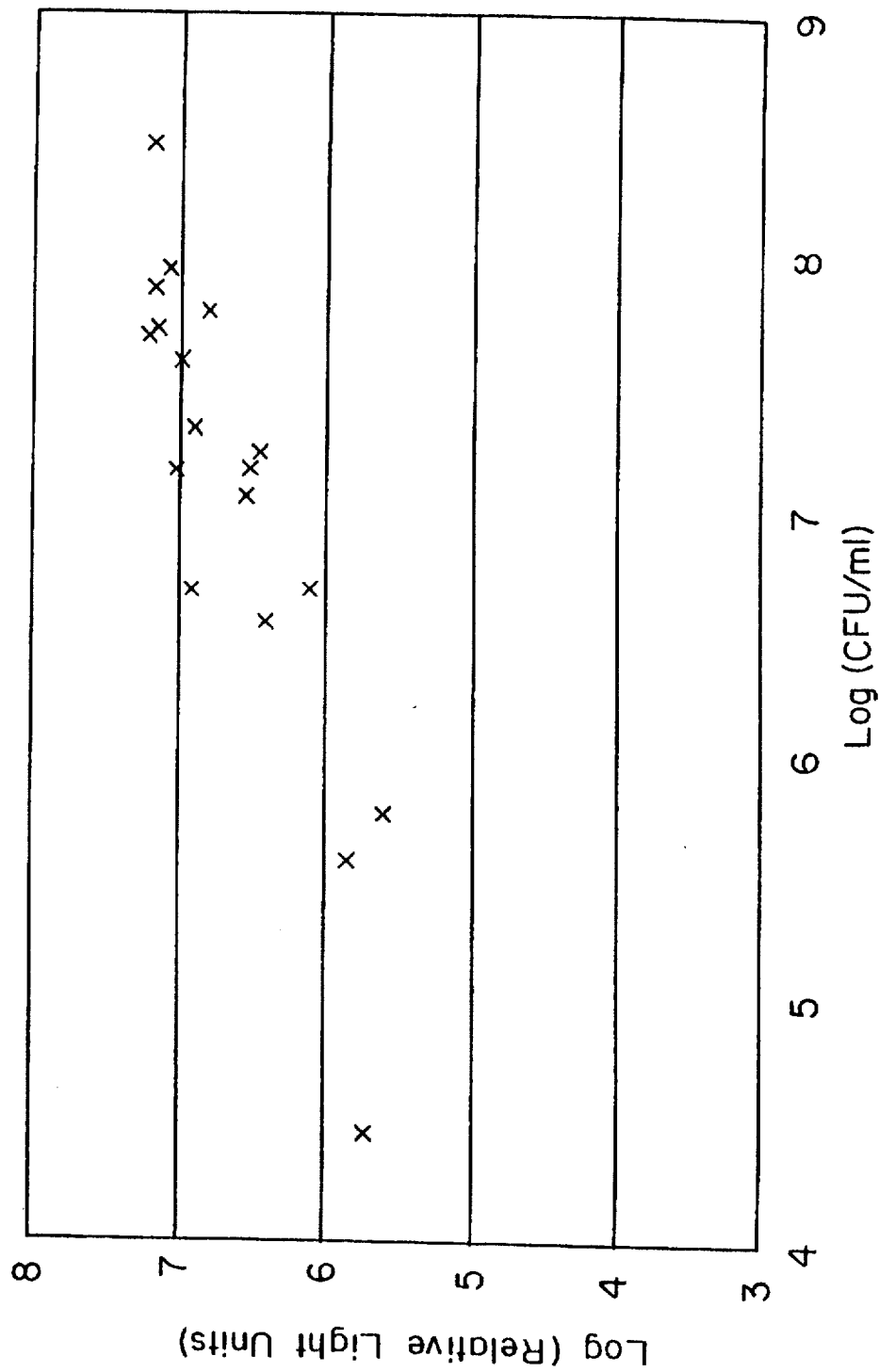

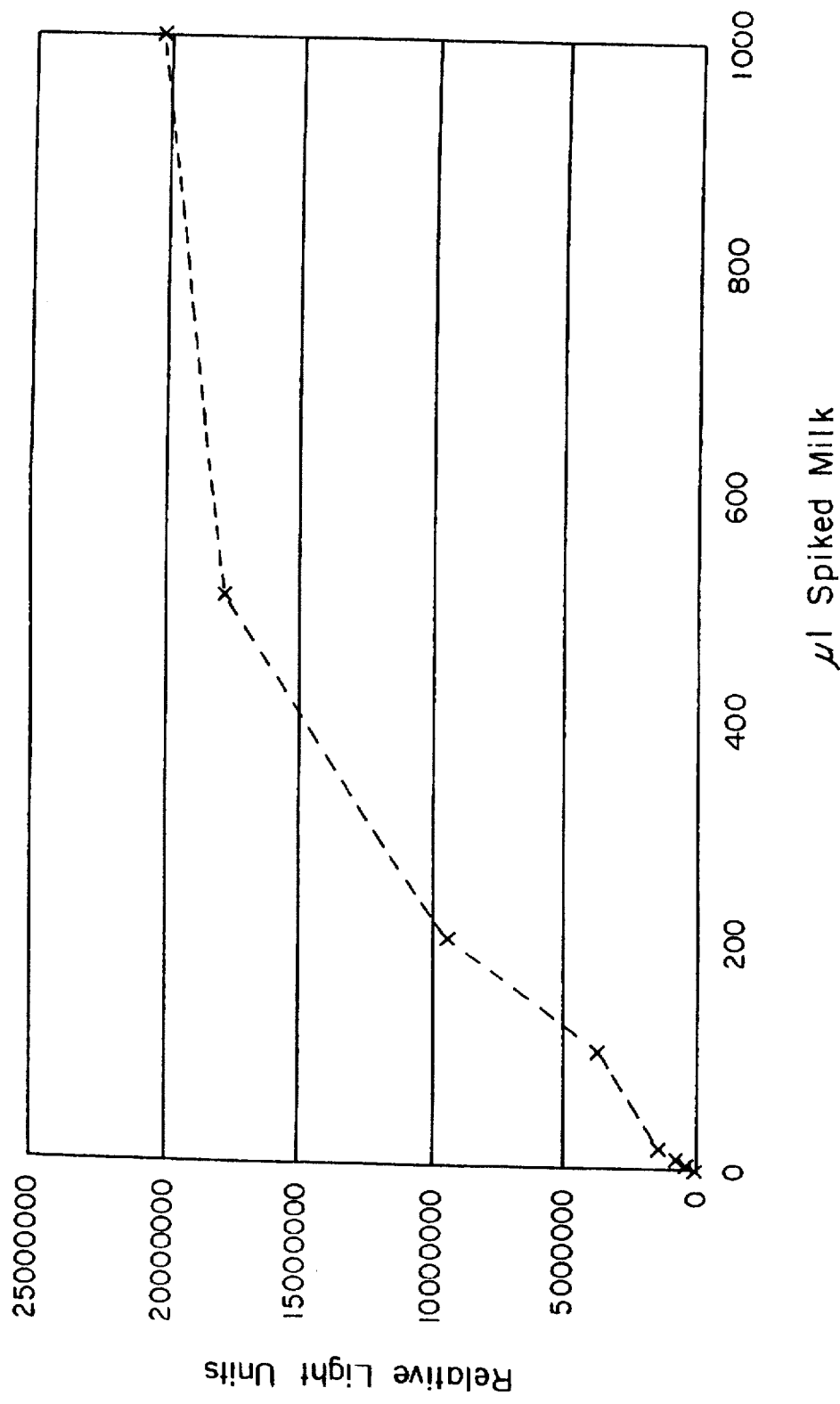

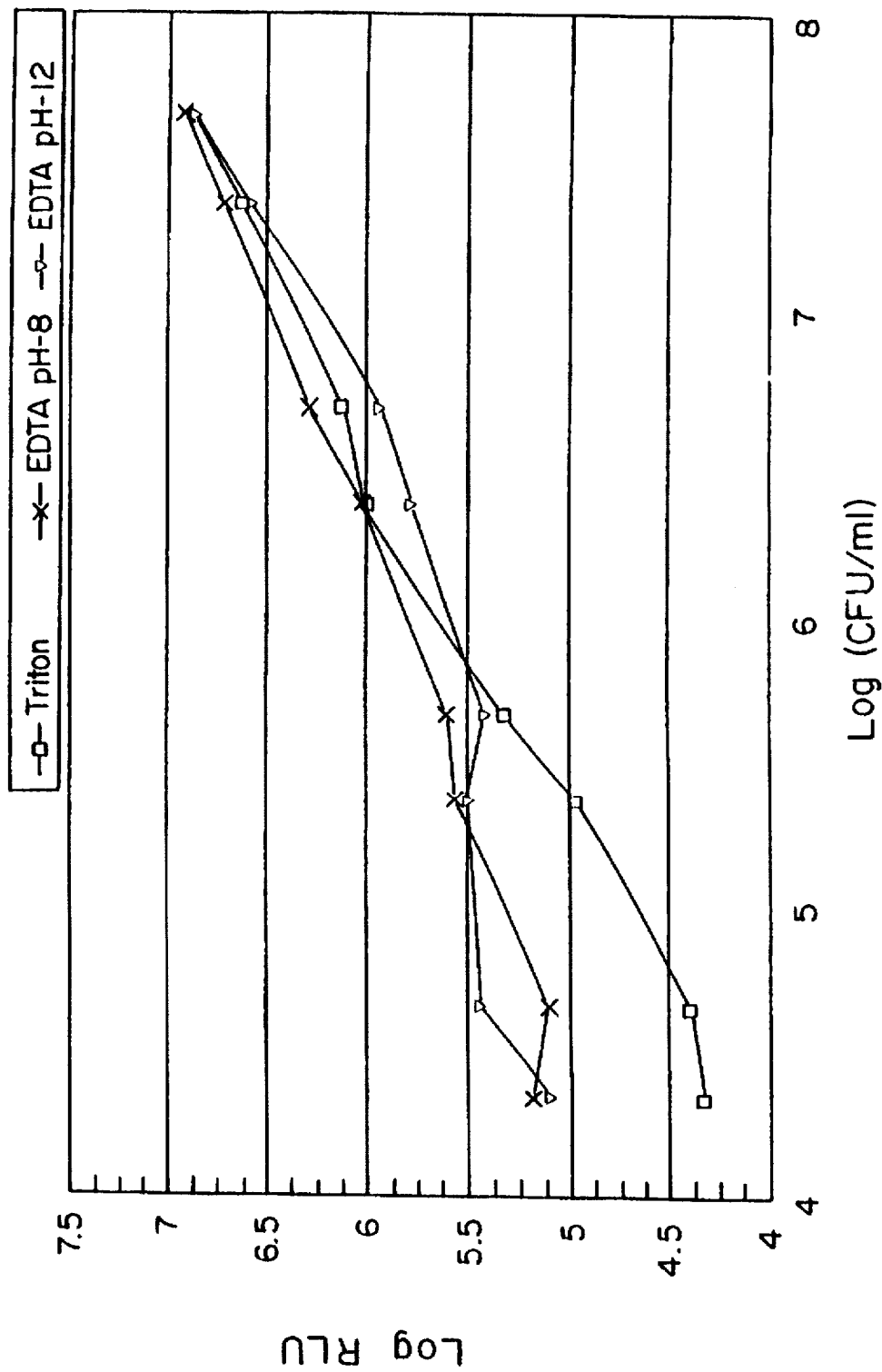
FIG. 9 Chelator Comparison Study

METHODS AND KITS FOR SEPARATION, CONCENTRATION AND ANALYSIS OF CELLS

RELATED APPLICATION

This is a divisional of U.S. patent application Ser. No. 08/003,242, filed Jan. 11, 1993 entitled METHODS AND KITS FOR SEPARATION, CONCENTRATION, AND ANALYSIS OF CELLS, now U.S. Pat. No. 5,587,286, which is a continuation-in-part of application Ser. No. 07/547,981, filed Jul. 2, 1990, now abandoned.

FIELD OF THE INVENTION

The present invention is generally directed to separating and concentrating cells from non-cellular components in a milk sample, such as raw milk, pasteurized milk or reconstituted powdered milk, or in cultures of microorganisms from other types of food, such as meat, or other sources, such as stool or blood, and then analyzing the separated cells, as for the presence of undesirable microorganisms.

BACKGROUND OF THE INVENTION

Procedures for counting or quantifying cells in milk samples fall into one of two categories. In the first category, bovine somatic cells in raw milk samples are counted by various means to identify milk producing animals that may have bovine mastitis, an undesirable condition which limits the quality and quantity of milk production in infected animals. Mastitis testing procedures include direct cell counting using automated instruments and bioluminescent somatic cell ATP determinations following cell lysis with agents such as detergents that release cellular adenosine triphosphate (ATP). The number of somatic cells originally present in the sample is estimated from the measurement of the ATP released.

In the second category, cells of simple, usually unicellular microorganisms, such as fungi and bacteria, referred to hereinafter collectively as "microorganism cells," are counted in milk samples using various counting procedures. These procedures are generally used in the assessment of milk quality, particularly to screen out grossly contaminated milk samples.

Of the procedures used for microorganism detection, the Breed Smear (Breed, R. S., Zbl. Bakt. Ilte. Abr. 30:337 (1911)) is generally the quickest method. In this technique, a milk sample is smeared onto a slide, dried, stained, and the bacteria are counted using microscopic examination. The drawbacks of this procedure are that both viable and non-viable organisms are counted, and if milk samples contain fewer than $10^5$ organisms/ml, many fields in the microscope must be counted to obtain statistically valid results. Microscopic evaluations are tedious and lead to operator fatigue.

The most widely utilized milk microorganism detection method is the standard plate method, which utilizes direct colony counting after plating in or on a growth medium. Standard methods (Standard Methods for the Examination of Dairy Products, 15th Ed., 1985, Richardson, G. H., Ed., American Public Health Org. Washington, D.C.) have been developed for milk samples, and many laboratories evaluate milk samples using either manual or automated plating procedures. While these methods have been utilized worldwide, there are certain disadvantages in using them. First, in the manual plating methods, two or more dilutions of the milk sample must be plated so that statistically significant plate numbers may be obtained. Second, plates for both the manual and automated plating procedures are usually incubated at elevated temperatures (e.g., in the U.S., 35° C.; in Japan, 32° C.); and, at these temperatures, the growth of psychrophillic organisms is repressed, yielding artificially low plate counting numbers. Finally, incubation periods of about 48 hours are required before bacterial plates can be counted and still longer plating periods are necessary for fungi. During this incubation period, bacterial numbers are increasing in the bulk milk from which the sample was taken, so that the result obtained is an underestimate of the actual number of colony forming organisms in the milk after the test. The delay in processing the raw milk to accommodate this incubation period by itself lowers the quality of the raw milk, and can contribute to shorter shelf lifetimes of the final product.

Plating or colony counting methods can be either manual or automated. Manual methods include the plate loop method (Thompson, D. I., Journal of Milk and Food Technology 30, 273 (1967)) and the Standard Plate Count, supra.

Semi-automated or automated colony counting methods include the Spiral Plating Method (Gilchrist, J. E., Appl. Micro. 25, 244 (1973)) and methods carried out by electronic colony counters (Fleming, M. G. Ir. J. Agric. Res. 14, 21 (1975)). The Direct Epi-Fluorescent Technique (DEFT) is a fluorescence-labeling technique which can be performed manually or with automatic instrumentation. Other techniques include impedance measurements after growth of milk organisms and radiometric procedures utilizing radioactive glucose.

Another approach to microbe evaluation has been the utilization of the bioluminescent measurement of ATP from living cells in milk using firefly luciferase (Lumac® bv, The Netherlands). In this scheme somatic bovine cells in raw milk are lysed with a detergent, which releases somatic cell ATP. This ATP from bovine cells, and any other non-microbial milk ATP, is degraded with an ATPase, usually potato apyrase. Finally, a bacterial lysing agent is added and bacterial ATP is measured in a bioluminescence assay using firefly luciferase. While much data has accumulated in the literature on these methods, the sensitivity has been inadequate for routine milk testing due to milk and extractant inhibition of the luciferase reaction, incomplete removal of non-bacterial ATP, deleterious effects of apyrase on bacterial ATP detection (Theron, D. N., J. Food Prod. 49:4–7 (1986)) both before and after bacterial cell lysis, and inefficient extraction of bacterial ATP. Literature data (Webster et al., J. Food Prod. 51:949–954 (1988)) for this type of assay suggest a cell sensitivity of approximately $1 \times 10^6$ cells/ml, which cannot be utilized in the United States where a cutoff for acceptance of $1 \times 10^5$ cells/ml for Grade A raw milk is required.

A logical improvement of this method that has been tried is concentrating the milk bacteria prior to the ATP assay. Various techniques have appeared in the literature which make use of cell filtration concentration (Peterkin and Sharpe, Appl. Environ. Microbiol., 39:1138–1143 (1980)), although these techniques are quite cumbersome, slow, and still exhibit most of the technical problems discussed above.

Lin et al., J. Dairy Science 72:351–359 (1989), describe a method of separating cells from various defined yogurt cultures grown in skim milk. In the method, 1% EDTA at pH 12 is added to the yogurt culture to bring the EDTA concentration to $\geq 20$ mg/ml of culture and the culture is centrifuged to separate a cell pellet. The cells of the pellet are then analyzed for β-galactosidase activity after being washed with phosphate buffer and disrupted by sonication.

There is no teaching in Lin et al. that the enzymatic activity which they measure is correlated to bacterial contamination of milk. Lin et al. do not teach a method of separating cells from, or a method for assessing bacterial contamination of, milk or any other food or material of biological origin.

While all of the techniques mentioned above have demonstrated some measure of success, none has proven to be inexpensive, simple, accurate, fast and sensitive enough to provide the milk industry with a type of test which can be used satisfactorily for routine testing.

Methods of assaying bacterial cultures grown from food (including milk and meat) samples for Salmonella contamination using an immunoassay technique, employing antibodies to an antigen common to Salmonella spp., and a nucleic acid probe hybridization technique, employing DNA probes for Salmonella DNA, are available. These methods, however, require cumbersome and time-consuming growth of bacterial cultures, from the food material being analyzed, before the assays for Salmonella can be carried out.

The need for such culturing prior to application of nucleic acid probe hybridization techniques to detect contamination, by undesirable microorganisms, of food materials, including milk, meat (e.g., chicken, turkey, beef, pork, horse, goat, whale and the like), eggs, fish, mussels, molluscs, crustaceans, vegetables, fruits, grains, and the like can be avoided, or the time for culture significantly reduced, if nucleic acid amplification techniques, such as the well known polymerase chain reaction (PCR) technique, are employed to increase the concentration of nucleic acid segments, characteristic of microorganism contaminants, to levels that are readily detectable by nucleic acid probe hybridization or nucleic acid staining methods. However, target nucleic acid amplification techniques have not been successfully applied for this purpose with cultures or extracts of specimens of food materials, or other materials of biological origin, such as blood, urine or stool, unless, prior to application of processes for amplification, microorganisms from the specimens have been subjected to cumbersome, costly, and otherwise undesirable, special treatments, such as with proteolytic enzymes, high concentrations of guanidinium salts, and detergent, or boiling, and the DNA from the microorganisms has been processed by similarly undesirable procedures such as ethanol-precipitation or chromatographic separation with or without phenol/chloroform extraction. These treatments have been regarded as necessary to separate nucleic acid, to be subjected to amplification, from contaminants, that interfere with the enzymatic reactions necessary for the amplification and that are thought to be provided by the microorganisms themselves or otherwise provided from the specimens to the microorganisms separated therefrom. See, e.g., Hill et al., Appl. Environ. Microbiol. 57:707–711 (1991); Keasler and Hill, Abstracts of the 91st General Meeting of the American Society for Microbiology, Abstract No. P-12, p. 269 (1991); Olive, J. Clin. Microbiol. 27:261–265 (1989).

SUMMARY OF THE INVENTION

The present invention provides a method for the concentration of cells, either mammalian or microorganism, from a liquid milk sample, which can be carried out in a simple and reliable manner. The present invention can be used to analyze various types of liquid milk products, including raw milk, pasteurized milk, reconstituted dry milk, cream, ice cream and other milk products and derivatives.

The method of the present invention comprises adding a chelating agent, usually in a solution referred to as a "clearing solution," to a milk sample, and then separating the cellular components from other milk components, such as by centrifuging the sample combined with chelating agent for a brief period of time, and separating or decanting non-cellular milk components from the separated cellular pellet. In a preferred separation method, involving centrifugation, microparticulate carrier, such as small polystyrene beads, that sediments slightly more slowly than the cells, is included in the sample during the centrifugation. An agent, such as a detergent, to lyse animal cells but not microorganism cells of interest, may also be included.

The components of the cellular pellet resulting from the separation are amenable to a variety of analyses, with such analyses being free from interferences that would be caused by contaminating milk components. For example, the cells of the pellet can be isolated in a manner that makes them amenable to quantitation using ATP bioluminescence techniques.

The cellular pellet may contain both somatic cells (i.e., mammalian cells from the mammal that is the source of the milk) and microorganism cells. Cells from the pellet can be microscopically examined to determine the relative concentration of somatic and microbial (i.e., microorganism) cells. The somatic cells may also be removed by adding a lysing agent, such as a detergent, to the sample with the chelating agent in the clearing solution, with an agent being chosen which lyses only the somatic cells. The pellet remaining after centrifugation will thus contain almost exclusively microbial cells, which can be analyzed in various ways, including analysis for ATP concentration after extracting ATP such as by lysing of the microorganisms. Filtration may also be utilized to separate cellular components from other milk components in the milk sample to which the clearing solution has been added.

The presence of animal cells, such as bovine somatic cells, in a raw milk sample, can also be determined in a quick and simple manner. The invention is further suited to the analysis of contamination of milk samples by a variety of microbes (microorganisms) such as bacteria, yeasts and molds, and spores from bacteria, yeasts and molds.

The present invention is also directed towards the utilization of concentrated cellular materials isolated from milk, or other foods or materials of biological origin, for various types of further analyses for undesirable contamination. Such analyses include those utilizing nucleic acid amplification by any of various methods, including polymerase chain reaction (PCR) methods, and those employing microscopic examination following use of dyes or stains, or other chromogenic, fluorescent, chemiluminescent or other detectable reporter molecules, to render observable cells to be detected. The invention is also directed towards the use of the concentrated cellular material for either broad spectrum or specific plating of microorganisms, or for preparation of samples in other forms, for any of the methods that have been utilized in the art for assessing bacterial or other microbial contamination of milk, other food stuffs, or other materials of biological origin.

The beetle luciferase ATP determination method (DeLuca, M. A., Advances in Enzymology, Meister, A., editor, 44, 37–68 (1976)) may be utilized in the present invention for quantification of cellular numbers in the original liquid milk sample. See, also, International Application Publication No. WO 92/04468. This ATP determination method is applicable to the quantification of either animal or microorganism cell numbers. Other methods that may be employed in accordance with the present invention for quantification of cell numbers in a liquid milk sample, or sample of other food or material of biological origin, are nucleic acid probe hybridization assay methods, including such assays following target nucleic acid amplification by PCR or other amplification techniques.

The method of the present invention may also be used as a pretreatment method for a variety of samples for centrifugation or filtration on various types of filtration matrices such as membranes, hollow fibers or centrifugation type filters.

While chelating agent, detergent (lysing agent), and microparticulate carrier each contribute important, independent advantages in the separation of cells from milk samples, in the case of other food samples the combination of microparticulate carrier with either centrifugation or filtration is sufficient.

Surprisingly, microorganism cells from milk samples, or from cultures or extracts of prepared from samples of other food materials, as indicated above, or non-food materials of biological origin, such as blood, urine and stool, after separation from non-cellular components using a chelating agent, microparticulate carrier/clearing solution (in the case of milk) or a microparticulate carrier/clearing solution (in the case of other materials) and separation method in accordance with the invention, are free of contaminants, other than those present in the separated cells themselves, that inhibit enzymatic reactions that are necessary for target nucleic acid amplification. Thus, advantageously, the separated cells can be used directly, without need for isolation of nucleic acid from other cellular constituents, to provide nucleic acid for amplification. The cells simply need to be treated (as by being held briefly at an elevated temperature) to cause them to release nucleic acid, and to denature enzymes or other components that would degrade amplified nucleic acid or inhibit enzymatic reactions required for the amplification method employed. If the amplification method relies on an enzyme that would be irreversibly inactivated at the elevated temperature, the cells can be added directly to a solution of reagents required for amplification, other than the temperature-sensitive enzyme(s), the solution can be heated to the elevated temperature and then cooled, and the enzymes can be added to initiate amplification (assuming target nucleic acid is present). In a preferred method, only thermally stable enzymes will be used in the amplification process (preferably PCR). Then separated cells are added directly to a solution with all reagents, including enzymes, required for amplification, and the solution is heated to an elevated temperature (low enough so that the enzymes for amplification remain active), and then, when the temperature is reduced sufficiently for primers to hybridize to template, amplification begins. Target nucleic acid segment from the microorganisms sought to be detected, if present, will be amplified in the amplification process. The nucleic acid resulting from the amplification process can then be assayed, using, for example, any nucleic acid probe hybridization assay method, for target nucleic acid segment.

Thus, the invention provides a method for testing milk products, other food materials, and other materials of biological origin, such as animal blood, urine or stool, for contamination by preselected microorganisms, characterized by having a particular target nucleic acid segment, comprising separating microorganism cells from the milk or other material of biological origin, or from a culture prepared with said material, using the cell separation methods of the invention (sometimes referred to as the cell wash methods); suspending microorganism cells so separated in a solution and treating the solution to provide nucleic acid from the cells for amplification without substantial isolation of nucleic acids of the cells from other constituents of the cells, subjecting the nucleic acid of the resulting solution to a nucleic acid amplification process, whereby target nucleic acid segment, if present, will be amplified or will cause the amplification of another, predetermined segment, and assaying the nucleic acid after the amplification process for the presence of amplified segment. The cells of the pellet yielded by the cell wash methods may be simply washed prior to being suspended in the solution for treatment to provide nucleic acid for amplification. Preferably the assay, which is the final step of the method, will be a nucleic acid probe hybridization assay, which, as the skilled will understand, will employ a probe (preferably an oligonucleotide and labelled to be detectable) capable of hybridizing to amplified target segment. As the skilled will understand, by carrying out the method in parallel with appropriate standards, the method can be used to not only detect the presence of preselected, contaminating microorganisms (if present at a level above the sensitivity of the method) in the material being tested with the method, but also quantify the extent of contamination of the material with such microorganisms. An elevated temperature, which can be used to release nucleic acid from cells and denature or inactivate amplification-inhibiting substances from the cells, is above about 70° C., and more preferably above about 90° C., for analysis of samples of cells from milk, or cultures prepared from meat, eggs, or aquatic species used as food sources.

In preferred amplification processes, aliquots of solution with reagents (e.g., enzyme) will not need to be added over the course of the amplification process. One preferred amplification method is the PCR method using a thermally stable DNA polymerase from a bacterium, such as *Thermus aquaticus*, which lives at high temperatures; in this method, thermal cycling will occur but the thermally stable polymerase will retain sufficient activity, notwithstanding the high temperatures reached in the cycling, that enzyme will not need to be replenished after each thermal cycle during the amplification process.

The present invention also encompasses novel kits for use in carrying out the methods of the invention. Such kits include a clearing solution, which, in the case of kits for milk samples, contains at least chelating agent and optionally microparticulate carrier or a somatic cell lysing agent, and, in the case of kits for other materials of biological origin, contains at least a microparticulate carrier. The kits also may contain a solution for washing or treating the cell pellet to lower the level of residual ATP background and, for ATP detection, a microbial cell ATP extracting agent or lysing agent, optionally a buffer solution, and an ATP detection reagent such as luciferase-luciferin. Kits may also include components for preparing a sample for the Breed Smear test or other types of direct microbiological examination procedures. Kits of the invention may also comprise enzymes, buffers, and other reagents for nucleic acid amplification or detection of amplified nucleic acid in a nucleic acid probe hybridization assay or by staining.

Further objects, features and advantages of the present invention will be apparent from the following detailed description when taken in conjunction with the accompanying drawings.

BRIEF DESCRIPTION OF THE DRAWINGS

In the drawings:

FIG. 4 is a graph showing the correlation between CFU and RLU for the separation of microbial cells from milk described in Example 3.

FIG. 6 is a graph showing the correlation between CFU and RLU for the separation of microbial cells from milk described in Example 5.

FIG. 7 is a graph showing the correlation between RLU and the amount of artificially inoculated milk in samples tested as described in Example 6.

FIG. 9 is a graph showing the correlation of RLU to CFU when different chelators or chelating conditions are employed as described in Example 10.

DETAILED DESCRIPTION OF THE INVENTION

Figure 1:
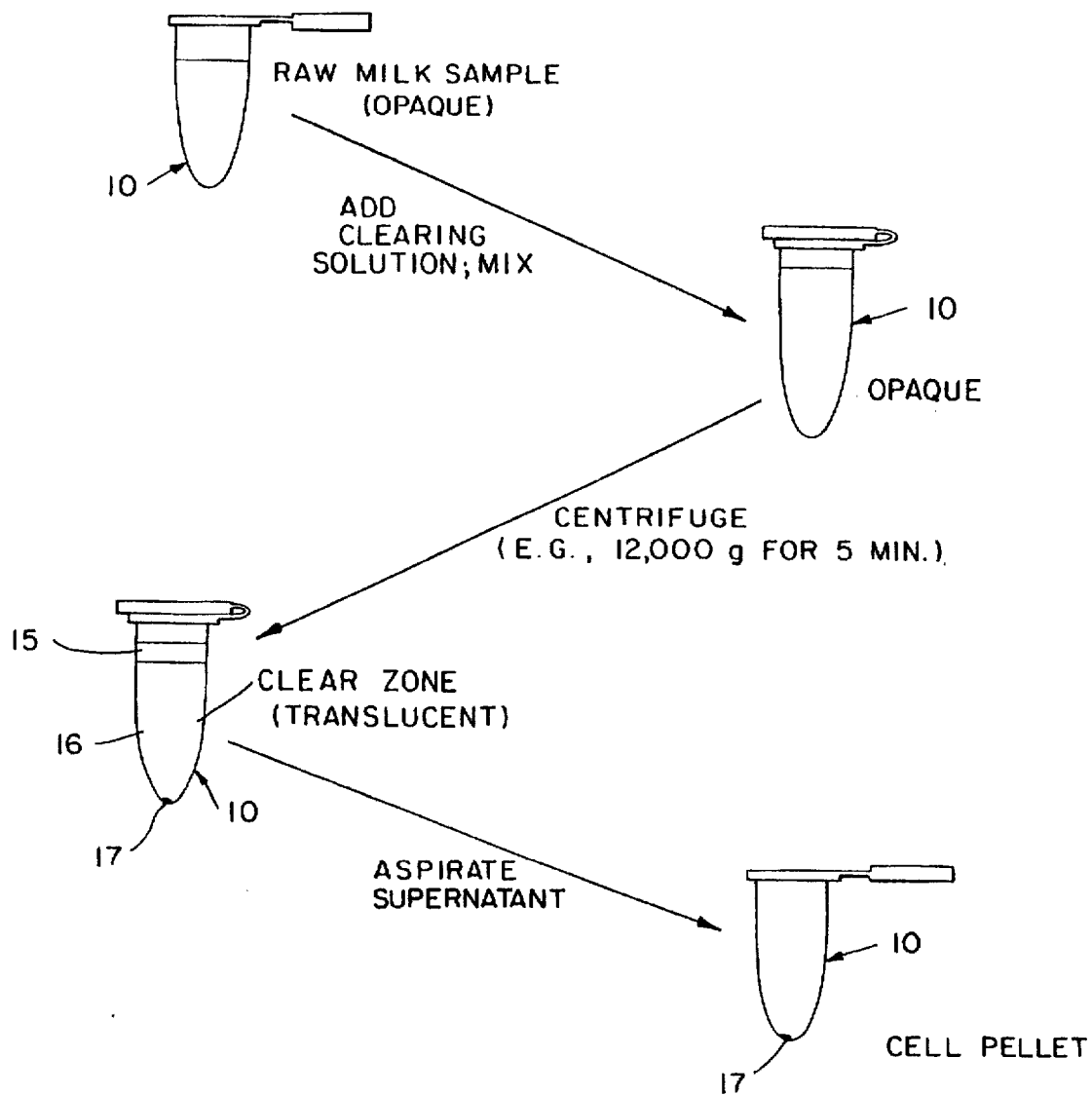
FIG. 1 illustrates the steps in the general method of the present invention using a liquid milk sample.

In general, the present invention is directed to a method for the separation and concentration of cellular materials from liquid milk samples or from cultures prepared from other food materials or from other materials, such as blood or stool, of biological origin. Cells are removed from milk samples or cultures by adding a clearing solution including a chelating agent, and optionally a microparticulate carrier such as polystyrene beads or an animal cell lysing agent such as a detergent, to the milk sample, and separating the cellular components from non-cellular components, such as by centrifuging the sample, and aspirating or decanting the non-cellular supernatant from the cellular pellet. The cells in the pellet can then be analyzed for, for example, microbial contaminants of the milk or other material.

The invention also encompasses a method for detecting the presence of cells, characterized by having nucleic acid that comprises a preselected target segment, in a culture or extract of a material of biological origin, said method comprising obtaining a pellet of cells from the culture or extract by combining an aliquot of the culture or extract with an aqueous suspension of a microparticulate carrier to form a clearing solution and centrifuging the clearing solution to form a cell pellet, provided that, if said culture of a material of biological origin is a liquid milk sample, said clearing solution further comprises a chelating agent; suspending cells from the pellet so obtained in a first solution and treating the first solution to provide a second solution of nucleic acid from the cells for amplification without substantial isolation of nucleic acids of the cells from other constituents of the cells; subjecting the nucleic acid of the second solution to a nucleic acid amplification process to provide a pre-determined, amplified nucleic acid segment only if the pre-selected target segment is present in said cells suspended from said pellet; and assaying nucleic acid after the amplification process for the presence of said pre-determined, amplified segment.

The invention also provides kits to carry out the methods of the invention.

The methods of the invention are preferably carried out with liquid milk samples.

Definitions:

The term "bacteria" is meant to include single-celled prokaryotes. It is also within the scope of the present invention to interchange the terms "microbe" or "microorganism cell".

The term "eukaryotic cells" is intended to denote organisms in which the genetic material is enclosed by a nucleus.

The term "liquid milk sample" is meant to include all liquid solutions of origin from dairy raw materials or products including raw milk, ultra high temperature pasteurized milk, low temperature long time pasteurized milk, reconstituted powdered milk, cream, skim milk, liquefied ice cream or ice milk or related products, and suspensions of milk or dairy products in liquid samples. While bovine milk is the preferred material for application of the present invention, the invention is applicable as well to milk from any mammal.

The term "chelator" or "chelating agent" is meant to include all molecules or macromolecules that bind to or combine with calcium ions and may also bind with other divalent metal ions including magnesium ion, iron ion, zinc ion, cadmium ion, beryllium ion, cobalt ion, nickel ion, copper ion, lead ion, and other metal ions. The term "chelator" or "chelating agent" includes all synthetic and natural organic compounds known to bind these ions, and any molecule of biological origin, or by-product or modified product of a molecule of biological origin, such as proteins, sugars or carbohydrates, lipids and nucleic acids, and any combination thereof, that may bind the above mentioned types of ions. The term "chelator" or "chelating agents" also includes any solid material of naturally occurring or synthetic origin that binds calcium and to a lesser extent magnesium and perhaps one or more of the other above-mentioned ions.

While various procedures utilized in the overall invention are generally known to the art, the combination of these procedures in accordance with the invention has not been contemplated. General methods known to the art, which play a part of the overall assay techniques of the present invention, include the standard plating techniques of microorganisms from dairy products, staining and identification methods for microorganisms, bacterial extraction methods, the use of separated, concentrated cellular materials in other procedures, and general chelating chemistry. A discussion of one or more of the above-noted techniques can be found in the following references, which are incorporated herein by reference: Standard Methods for the Examination of Dairy Products, 15th Ed., 1985, Richardson, G. H., Ed.; American Public Health Assoc., Washington, D.C.; Bacteriological Analytical Manual, 6th Ed., United States Department of Agriculture (USDA), 1984, Marcel Dekker Inc., New York; Sambrook J., Fritsch, E. F., and Maniatis, T., Molecular Cloning, 2nd Ed., Ferguson, M., Ed., Cold Spring Harbor Laboratory Press, 1989; O'Connor, F., Australian J. Dairy Tech., pp. 61–65 (June, 1984) (this reference includes descriptions of microbiological milk testing methods and relevant references for each method); Karl, Microbiological Reviews 44, 739–769 (1980); Martell, A. E., Chemistry of the Metal Chelate Compounds, Prentice-Hall, New York, 1952; Current Protocols in Molecular Biology, John Wiley & Sons, New York, New York, 2 volumes (supplemented) (1987–1992).

As indicated in the cited Molecular Cloning and Current Protocols in Molecular Biology, nucleic acid amplification techniques, particularly those with thermally stable enzymes, such as PCR amplification employing DNA polymerases from *Thermus aquaticus*, are well known, as are nucleic acid probe hybridization assay methods and staining methods for detecting nucleic acid segments. Additional information on such techniques can be found in U.S. Pat. Nos. 4,693,195 and 4,693,202 (PCR and its application in nucleic acid probe hybridization assays for diagnosis); International Patent Application Publication No. WO 88/10315 (transcription-based nucleic acid amplification/detection methods); U.S. Pat. No. 4,889,818 and International Patent Application No. PCT\US90\04169 (published February, 1991)(thermostable DNA polymerases from *Themus aquaticus* (Taq DNA polymerases) and their use in PCR amplification); European Patent Application Publication No. 0 329 822 (isothermal transcription-based nucleic acid amplification process); U.S. Pat. No. 4,957,858 (Q-Beta replicase catalyzed autocatalytic replication of replicatable RNA linked to probes complementary to target segment).

The present invention encompasses a separation and concentration technique for the removal of cellular materials from liquid milk samples and other cultures. While the technique will now be described with reference to a liquid milk sample, it will be understood that it may be applied as well to cultures prepared from other materials.

In carrying out the technique, a milk sample is placed in an appropriately sized centrifugation vessel as shown at 10 in FIG. 1 and a chelating agent, and optionally a microparticulate carrier or a lysing agent, are added. The chelating agent may be one of various types as described above, which by way of illustration only, may include ethylenediamine tetraacetic acid (EDTA, Versene®), bis(o-aminophenoxy) ethane-N,N,N$^1$,N$^1$-tetraacetic acid (BAPTA), ethyleneglycol-bis-(β-aminoethyl ether)N,N,N$^1$,N$^1$-tetraacetic acid (EGTA), nitrilotriacetic acid (triglycine, ammonia triacetate, Trilon A or, herein, simply "Trilon"), trans-1,2-diaminocyclohexanetetraacetic acid (CDTA), diethylenetriaminopentaacetic acid (DTPA), N-(2-acetamido) iminodiacetic acid (ADA), citrate, arginine, hypoxanthine, 4,5-dihydroxybenzene- 1,3-disulfonic acid, sodium phosphate glass or any of the molecules in the "glass" or polyphosphate family, crown ether type compounds and all derivatives and precursors of such molecules.

Among the chelators that may be employed are nitrilotriacetic acid and derivatives thereof, of Formula I (HOOC(CH$_2$))$_2$NR$_1$    I wherein R$_1$ is selected from the group consisting of —(CH$_2$)COOH; —(CH$_2$)CONH$_2$; —(CH$_2$)CO(CH$_2$OH); —(CH$_2$)(CO)COOH; —(CH$_2$)(CO)COCH$_3$; —(CH$_2$)(CO)(CH$_2$)COOH; —(CH$_2$)(CO)(OCH$_2$CH$_2$)$_q$OH, wherein q is an integer from 1 to 30;

wherein R$_2$ is selected from the group consisting of —COOH, —NH$_2$, and —N((CH$_2$)COOH)$_2$; —(CH$_2$)(S(O)$_r$)CH$_3$, wherein r is 1 or 2; —(CH$_2$)SO$_3$H; —(CH$_2$)(S(O)$_r$)(CH$_2$)COOH, wherein r is 1 or 2; —(CO)CH$_2$COOH; —(CO)COOH;

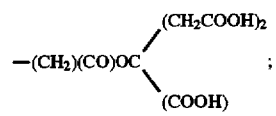

—(CH$_2$)(CO)OR$_3$, wherein R$_3$ is selected from the group consisting of phenyl substituted at any one position with hydroxyl,

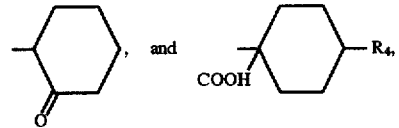

wherein R$_4$ is selected from the group consisting of H, —COOH, —CONH$_2$, —OH, and —SO$_2$H;

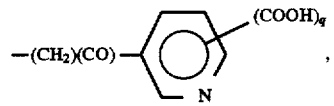

wherein q is an integer of 1 to 4 (i.e., the pyridine ring is substituted at 1 to 4 positions with —(COOH)); —(CH$_2$)(CO)(CH$_n$(X$_1$)$_m$), wherein m and n are both integers from 0 to 3, m+n=3, and X$_1$ is selected from the group consisting of —Cl, —Br, —F, —CN and —NO$_2$; —(CH$_2$)(CHOH)$_p$ (CH$_2$OH), wherein p is an integer from 0 to 9; —(CH$_2$)(CO) (C(X$_2$)$_2$)(CO) C(X$_2$)$_3$, wherein X$_2$ is selected from the group consisting of —H, —Cl, —Br, and —F; and —(NH)(CO) (CH$_2$)COOH.

As the skilled will understand, various salts (e.g., sodium salts) and anionic forms of the chelating agents described herein as acids will be employed in carrying out the invention.

The chelating agent, for example EDTA, Trilon or ADA, and carrier or lysing agent, if present, are preferably added to the milk sample together in a solution, called a "clearing solution"; and the mixture of chelating agent, and carrier or lysing agent, and milk sample is capped and inverted or vortexed to mix. The sample is then placed into a centrifuge of appropriate size, and the sample centrifuged at 10,000×g (minimum relative centrifugal force) for a minimum of 5 minutes. After centrifugation the sample separates into three distinct phases. The uppermost phase is a cream and milk protein "pad" illustrated at 15 in FIG. 1, and this pad floats at the very top of the liquid sample. Beneath the pad is the second "clear" liquid zone, illustrated at 16 in FIG. 1, which is, unlike a milk sample, non-opaque and translucent. Finally, at the bottom of the centrifuge tube is the cellular pellet 17, the size of which is dependent on the number of cells in the original milk sample and the type of chelating agent(s) and/or microparticulate carrier and/or detergent(s) used in the treatment. The pellet may also contain a small amount of other milk components which are associated with the cells. After clearing of a typical 1.0 ml raw milk sample, the pellet is approximately 10 to 40 µl in volume and is white or off-white in appearance.

The proposed effect of the chelating agent in the present invention is the dissociation of casein micelles in a milk sample into "sub-micelles" (Chaplin, J. Dairy Res. 51:251–257 (1984)). After the chelating treatment, micellular milk protein material rises to the top of a centrifuge tube or remains in solution, as opposed to pelleting in the absence of chelator. The chelator binds calcium ion which is a major component that contributes to micelle structure (Lia, Biochemistry 11:1818–1821 (1972)). Thus, chelating agents that bind calcium ion particularly well are preferred in the present invention.

The ideal chelator, for the isolation of cells to be quantitated using measurement of ATP by bioluminescence, must fulfill two requirements. The first requirement is the separating capability mentioned above to reduce nonmicrobial ATP background to acceptable levels. The second requirement which must also be met is the maintenance of microbial ATP pools for subsequent determination and quantification. Chelating/centrifugation procedures previously described (Lin, et al. (1989), supra) do not meet this second requirement because EDTA chelating at high pH levels (pH12) significantly reduce bacterial ATP levels. A chelating agent that can simultaneously reduce milk ATP background, while maintaining microbial ATP pools is highly preferred in the present invention and particularly in applications of the invention where ATP is to be measured to assess microbial concentration or contamination. In this regard, chelating agents which have been found to be particularly suitable are nitrilotriacetic acid and N-(2-acetamido) iminodiacetic acid.

However, ethylenediamine tetraacetic acid is preferred as a chelating agent in applications of the invention where nucleic acid amplification is carried out with nucleic acid from the separated cell pellet and then microbial concentration or contamination is assessed by a nucleic acid probe hybridization assay with the amplified nucleic acid.

The present invention may also employ microparticulate carrier for the collection of cells, especially microbial cells, during the centrifugation steps of the cell separation process. The microparticulate carrier serves to assist in the pelleting process. The physical nature of the microparticulate carrier is such that the carrier sediments, or pellets, slightly slower than the microbial cells and as such makes the cell collection more quantitative.

A number of materials could be used as microparticulate carriers, including "beads" of polystyrene, latex, plastic, glass, diatomaceous earth, metal oxides, and colloidal materials including polyacrylamide, dextrans, cross-linked dextrans, and starches. The properties of the microparticulate carrier that are desirable are threefold: 1) The carrier should sediment as fast as, or preferably slightly slower than, the cells of interest that are being collected. This characteristic is basically a function of the particles' density, size and charge. 2) The carrier should be amenable to resuspension after centrifugation for the purpose of facilitating treating or evaluating the cell pellet. 3) The carrier must be inert to the testing or evaluation that will be performed on the cell pellet. For example, the carrier should be invisible in cell-staining techniques if a microscopic examination is to be performed, or the carrier should not bind an analyte, such as ATP, that will be measured to measure or estimate numbers or concentrations of microbial cells. Beads of materials cited above with diameters between about 0.25 µm and 2.5 µm are suitable as microparticulate carriers. Surfactant-free polystyrene beads with a diameter from 0.5 to 1.5 µm are the preferred microparticle carriers.

The use of microcarrier particles in the cell separation method of the invention enhances the ease with which an operator is able to remove unwanted supernatants from cell pellets following a centrifugation. The carrier serves as a visual indicator much larger than the microbial cell pellet and as such makes the removal of the supernatants much more convenient. In addition, the probability of mistakenly aspirating part or all of the cell pellet is greatly reduced when a microparticle carrier is used.

If one wishes to remove somatic cells from a raw milk sample and separate out and concentrate only microbial cells, a somatic cell lysing detergent, such as non-ionic detergents Triton X-100, Nonidet P-40 (NP-40), or the like, may be added to the milk sample in combination with the chelating agent. Such a detergent will specifically lyse bovine somatic cells (animal cells) without lysing microbial cells. Because the somatic cells are lysed in the treatment prior to centrifugation, there will be essentially no intact somatic cells in the post-centrifugation pellet. Subsequent ATP determinations made on these pellets will thus detect only the bacterial cells or other microbe cells.

If, on the other hand, one wishes to measure or quantify the number of somatic cells in a milk sample, a somatic-cell lysing detergent, such as one of those mentioned above, can be added to the cellular pellet and only somatic cells will be lysed. A cellular metabolite such as ATP which was contained in the somatic cells can then easily be measured without any elevation of the result by microbial ATP, which cannot be extracted with the somatic-cell-lysing detergent. The number of somatic cells that were present in the sample can then be calculated using the known amount of ATP that was measured and the average amount of ATP known to exist in somatic cells. This procedure is an improvement over previously published methods (R. Bossuyt, Milchwissenschaft 33:11–13 (1978)).

The present method provides a useful procedure for concentrating cells and eliminating background milk contaminants such as casein and casein micelles, lipophilic components, and salts. To perform this concentration, milk, for example one ml, is cleared by centrifugation with a chelating agent, and the resulting pellet is resuspended in a very small volume (for example, 10 µl) of the appropriate buffer or liquid. In this example, all of the cell components are removed from the milk contaminants and are concentrated 100-fold. This concentrated sample can then be utilized in other analyses as desired.

One example of the usefulness of this procedure is in staining and counting microorganisms from raw milk. If a milk sample contains less than $1 \times 10^5$ organisms per ml, and 10 µl of milk is put onto a microscope slide and stained, many fields of the stained specimen must be viewed in order that statistically significant counting data be collected. The fields are difficult to score because of background staining of other milk components. This procedure, the Breed Smear procedure, is widely used, particularly in Japan, for raw milk quality assessment. By utilizing the foregoing concentration step (100 fold concentration) many fewer fields need to be counted and fields are much easier to score because the background is much clearer. This speeds up specimen throughput and reduces operator fatigue and error.

Somatic cell numbers in a specimen may be quantitated by separating all cells from the various other components of milk and concentrating the cells in accordance with the present invention.

Microbial cells in a pellet, which is free from contaminating somatic cells by virtue of use of a somatic-cell-lysing detergent as outlined above, can be lysed with a microbial extracting agent and assayed for ATP. The number of microbial cells is then estimated using the ATP measurement and the average amount of ATP known to exist in microbial cells or, more specifically, in milk microbial cells. This type of procedure offers a number of advantages over other methods such as standard plating and spiral plating. First, it is much faster, because a result is available in as little as 15 minutes, and consistently in under an hour, as opposed to the 48 hour time frame for the standard plating and spiral plating methods. Second, the ATP measurement will give results that are not influenced by cell clumping, i.e., ATP will be measured from all cells; in plating methods cell pairs or groups of cells are scored as a single cell because one colony is formed. Third, the ATP method will measure ATP from psychrophillic organisms which will be missed in plate counting methods that culture at temperatures over 30° C.

As mentioned before, cells which are separated and concentrated using the present invention can be subjected to various other methodologies (e.g., treatment with a protease, such as α-chymotrypsin, and/or an ATPase such as an apyrase) with the background greatly reduced and the cell number (and associated signal) greatly increased due to concentration. This provides the possibility of greater sensitivity, and more reliable, reproducible results due to background elimination.

A method of the present invention may also include cell enrichment or enhancement techniques either before or after the clearing centrifugation so that sensitivity, cell number, or cell hardiness may be improved. For example, by treating cells with treatments (Theron, J. Food Prot. 46:196–198 (1983)) or components (K. M. Oxley, Bioluminescence and Chemiluminescence, Ed. J. Scholmerich, John Wiley & Sons, N.Y., pp. 495–198 (1986)) that increase cellular ATP, the sensitivity of the procedure may be enhanced. This type of procedure can also be applied to detecting specific types of cells in a particular sample, using selective media or even polyclonal or monoclonal antibodies.

Persons of skill in the art are well aware of the need for, and nature of, appropriate controls in assay procedures of the type employed in the present invention and appropriate standards to allow quantitative information on analyte concentration or quantity to be determined from such assay procedures. Such controls and standards are illustrated in the following Examples.

Reference is now made to FIG. 1, where the clearing wash method of the present invention is illustrated with reference to a milk sample. In this procedure, a milk sample is first placed into a centrifugation vessel 10. Next, a chelating agent, plus (preferably) or minus microparticle carrier, and plus or minus a somatic cell lysing detergent, is added using a clearing solution, as indicated. The contents of the vessel are mixed, the vessel is then centrifuged, and the resulting sample is said to be "cleared". If a milk sample without a chelating agent were to be centrifuged in the same manner, there would be no "clearing" but a large, diffuse, milk protein and cell pellet at the bottom of the tube. Finally, the cell pellet is freed from most of the other materials in the vessel by aspiration of the supernatant after the centrifugation. The addition of the microparticle carrier greatly assists in the collection of microbial cells, and in the aspiration and removal of non-microbial milk components.

Kits for the analysis of cellular components from liquid milk samples can be formed of the following components:

A microbial test kit using ATP detection comprises:
  (a) A clearing solution containing a chelating agent, a somatic cell lysis detergent such as the chelating agents and detergents described above, and, optionally and preferably, a microparticulate carrier.
  (b) Optionally, a solution for washing or treating the cell pellet.
  (c) An ATP extractant such as a cell lysis solution, as described above, for releasing microbial cell ATP.
  (d) Optionally, a buffer solution.
  (e) An ATP detection reagent, such as luciferase (e.g., from P. pyralis)-luciferin for measurement of ATP by bioluminescence.

A microbial test kit using the Breed Smear comprises:
  (a) A clearing solution as described for the microbial test kit using detection of ATP.
  (b) Optionally, a solution for washing the cell pellet.
  (c) A solution for staining cells.

A bovine somatic cell test kit using ATP detection comprises:
  (a) A clearing solution as described above for the microbial test kit using detection of ATP, excluding the somatic cell lysis detergent.
  (b) A somatic cell lysis solution that does not lyse microbial cells.
  (c) An ATP detection reagent such as luciferase-luciferin.

A microbial detection kit for detection of microorganisms via nucleic acid amplification and nucleic acid probe hybridization comprises:
  (a) A clearing solution which comprises a microparticulate carrier and, in the case of a milk sample, will also comprise a chelating agent.
  (b) Optionally, solution for washing the cell pellet from the cell wash method using the clearing solution.
  (c) Enzymes and primers required for amplification of a target nucleic acid segment characteristic of the microorganisms to be detected. Optionally, other, more commonly available components used in the amplification, such as nucleoside triphosphates (2'-deoxyribonucleoside triphosphates in case only DNA is synthesized in the amplification process), buffers, and the like may be provided.
  (d) Nucleic acid probe for target segment amplified with the components in (c) together with reagents required to detect probe hybridized to said target segment, if the probe per se is not detectable (e.g., as labelled with $^{32}P$). For example, if the probe is labelled covalently (i.e., directly) with an enzyme, such as alkaline phosphatase, or non-covalently (i.e., indirectly), through biotin covalently linked to the probe, with an avidin-enzyme (e.g., alkaline phosphatase) complex, wherein the enzyme catalyzes production of a chromophore, which provides the detected signal, then reagent for production of the chromophore and, for indirect labeling, avidin-enzyme complex will be provided. Again, buffers, solid supports for hybridization, and the like may also be provided.
  (e) Alternatively, or optionally in addition, to nucleic acid probe and associated reagents as in (d), a staining reagent such as ethidium bromide to detect amplified target of known size, as on a gel. Reagents for preparing a suitable gel, running in parallel a sizing gel, and the like may also be provided, as the skilled will understand.

Each of the foregoing kits may optionally include a filter, for example, as described in Example 6 below, and reagents to provide suitable controls or, for quantification, standards.

The invention is further illustrated by the following, non-limiting examples.

EXAMPLE 1

This example discloses the separation of microbial cells from an artificially inoculated milk sample. In addition, the assay is compared to a commercially available milk ATP assay to compare the relative sensitivities of the two procedures.

Raw milk samples were obtained from a local dairy and the raw milk was streaked on standard methods agar (Standard Methods for the Examination of Dairy Products, supra) to isolate individual colonies. Eleven visually different colony types were picked and gown in standard methods broth in an attempt to obtain a representative sample of the different species that may be found in raw milk. Of these isolates one cell type (Serratia liquefaciens) was chosen for the experiment.

A pasteurized milk sample was used as a negative control for the procedure. To one ml of this pasteurized milk was added 10 µl of the overnight grown (23° C.), milk-isolated bacteria (*S. liquefaciens*). Using this artificially inoculated milk sample and uninoculated pasteurized milk, a number of inoculated milk samples were prepared as set forth in Table 1 below.

TABLE 1

| Tube | Pasteurized Milk (µl) | Inoculated Milk (µl) |
|---|---|---|
| 1 | 1000 | 0 |
| 2 | 999 | 1 |
| 3 | 998 | 2 |
| 4 | 995 | 5 |
| 5 | 990 | 10 |
| 6 | 980 | 20 |
| 7 | 950 | 50 |
| 8 | 900 | 100 |
| 9 | 800 | 200 |
| 10 | 500 | 500 |
| 11 | 0 | 1000 |

To calculate the number of organisms put into the inoculated milk sample, 100 µl of serial dilutions ($10^{-3}$, $10^{-4}$, $10^{-5}$, $10^{-6}$, $10^{-7}$, and $10^{-8}$) at the overnight cell suspension were plated on standard methods agar and incubated overnight at 37° C. The resulting colony counting data was used to calculate the number of bacteria in tubes 2–11.

A series of eight 1.5 ml micro-centrifuge tubes were placed into a test tube rack and numbered, and 1.0 ml of each of the samples 1–8 in Table 1 was placed into each tube. The milk was incubated at room temperature (22° C.) for 10 minutes, and 500 µl of a 0.25M EDTA, pH 8.0, 0.5% Nonidet P-40 (NP-40) solution was added to each tube. The tubes were capped, inverted 10 times to mix, and placed into the rotor of an angle head microcentrifuge (Wheaton) being careful to have the tube hinges pointing outward. The tubes were centrifuged at 12,000×g for 10 minutes and the supernatant was then carefully removed using a 1000 µl disposable piper tip which was attached to a faucet aspirator. The tube was tipped slightly to pour the last remaining supernatant into the aspirator, so as not to aspirate, or otherwise disrupt, the resulting pellet.

To each pellet 500 µl of a 0.1M $MgCl_2$, 0.2% NP-40 solution was added, the tubes were capped and vortexed to resuspend the cells in the pellet, and then the tubes were centrifuged as before. After centrifugation, the supernatants were again aspirated and another 500 µl of 0.1M $MgCl_2$, 0.2% NP-40 was added to each tube. The tubes were capped, centrifuged and aspirated as before.

To each tube was added 50 µl of a 1% trichloracetic acid (TCA), 1 mM EDTA, 0.0005% xylenol blue solution to extract the cellular ATP. The tubes were vortexed and allowed to incubate for 10 minutes at room temperature.

Using disposable plastic piper tips, the TCA extracts were transferred to luminometer cuvettes (Sarstedt) and neutralized with 400 µl of a 0.1M Tris-acetate buffer, pH 7.75. To initiate the luciferase reaction, 100 µl of a P. pyralis luciferase-luciferin reagent (Promega Corp., Madison, Wis., U.S.A.) was added, and the light output measured using a Berthold 9501 luminometer (Berthold Analytical, Munich, Germany) using a 10 second integration time. Light output results are printed out as relative light units (RLU).

Using equivalently prepared contaminated milk samples (Tubes 1–11 listed in Table 1 above), 50 µl samples of each milk sample was analyzed using a commercially available milk bacterial detection kit ("LUMAC®" bv, The Netherlands) using the manufacturer's protocol.

Figure 2:
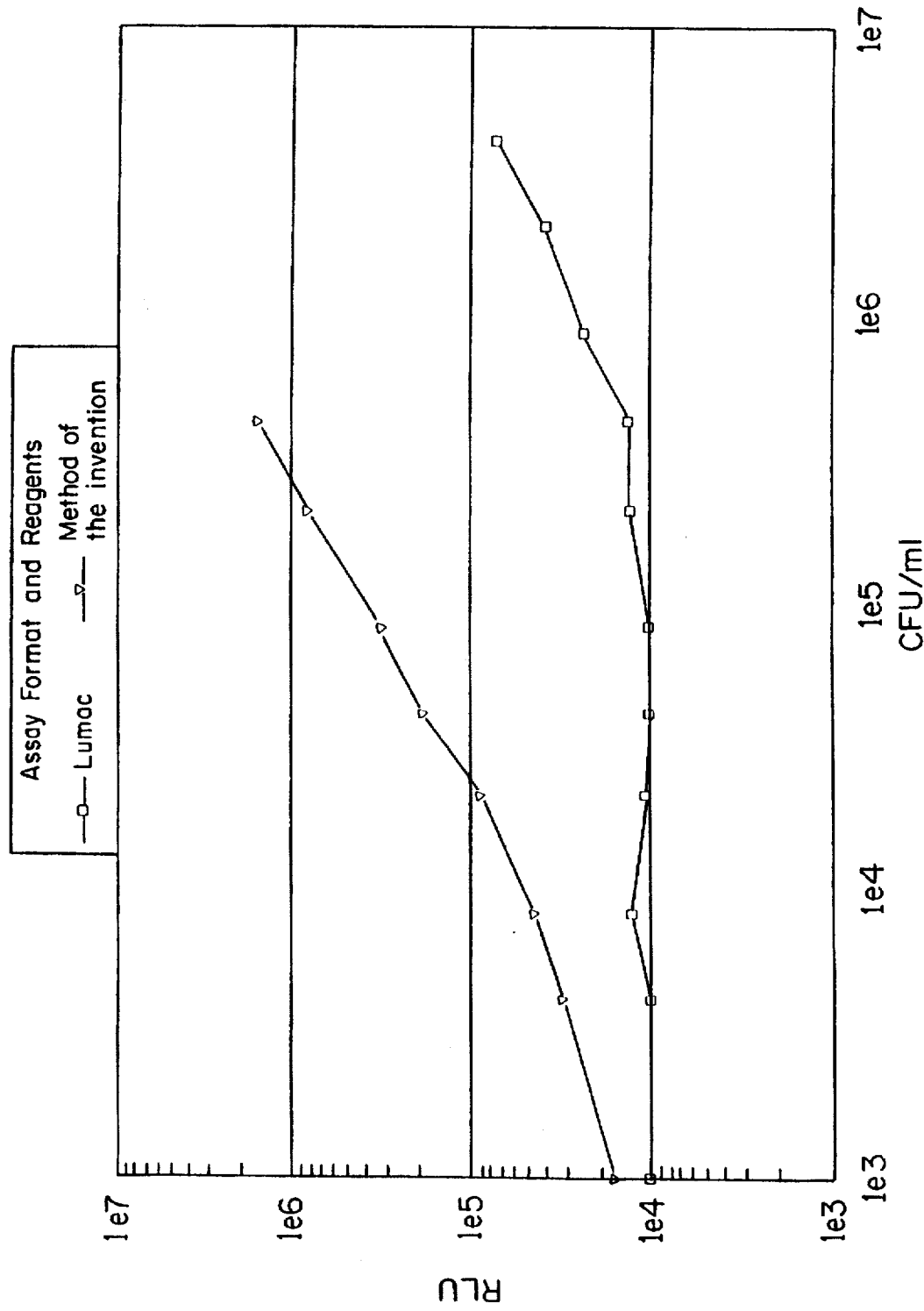
FIG. 2 is a graph showing plots of relative light units (RLU) in samples analyzed in accordance with the present invention and by another procedure versus the concentration of microorganisms in the samples as described in Example 1.

Results from these assays are summarized in FIG. 2. Log of RLU (y-axis) is plotted versus log of bacterial number (x-axis) in colony forming units (CFU) per milliliter for the present invention and the commercially available milk assay kit. Sensitivity for the present invention was found to be less than $1\times10^4$ cells/ml while the sensitivity for the Lumac assay was approximately $1\times10^6$ cells/ml.

EXAMPLE 2

This example discloses the separation of microbial cells from eleven raw milk samples and one pasteurized milk sample.

Raw milk samples were received from a local dairy and stored at 4° C. A pasteurized milk sample was also included in the study. One ml of each milk sample was pipetted in duplicate into 1.5 ml Eppendorf tubes. The milk samples were allowed to incubate at room temperature for 10 minutes followed by the addition of 0.5 ml of 0.5% NP-40, 3% nitrilotriacetic acid (sodium salt) to each tube. The tubes were then capped and mixed by inverting 10 times.

The tubes were centrifuged at room temperature for 5 minutes at 12,000×g and the supernatants aspirated as in Example 1. To each pellet 0.5 ml of a 0.05 mM $MgCl_2$, 0.2% NP-40 solution was added, the tubes were capped and vortexed, and centrifuged for 5 minutes as before. After centrifugation the supernatants were again aspirated, and the washing, centrifugation and aspiration were repeated one more time.

The pellets obtained were treated with TCA solution and read in a luminometer, as described above in Example 1. For each sample, the result is determined as the mean of the duplicate measurements.

Each milk sample was also diluted with sterile 0.8% NaCl and 1.0 ml of 10-fold dilutions were piperted into duplicate petri dishes. Approximately 20 ml of sterile standard methods agar was added to each dish and mixed. The. plates were incubated at 23° C. for 48 hours and colonies were then counted. Results are the means of duplicate plate counts.

Figure 3:
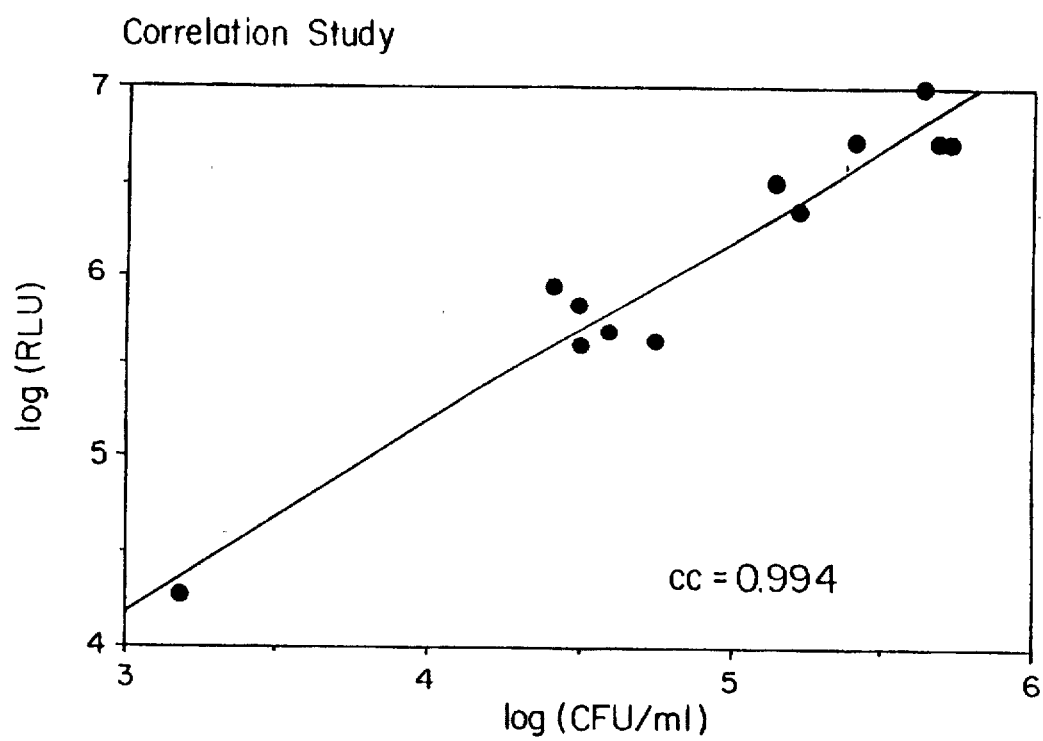
FIG. 3 is a graph showing the correlation between colony forming units (CFU) and RLU for the separation of microbial cells from milk described in Example 2.

The results of this example are shown in FIG. 3. A linear response between log colony forming units (CFU)/ml and log RLU is obtained over the range studied. The correlation coefficient for this data was 0.994, indicating a significant relationship between the two methods.

EXAMPLE 3

This example discloses the separation of microbial cells from 65 raw milk samples using a modification of the procedure presented in Example 2.

The milk samples were treated as in Example 2, with an additional step of adding a protease treatment to treat the microbial pellet.

After the first centrifugation step the resulting pellet was dissolved in 500 µl 0.05 mM $MgCl_2$, 0.2% NP-40, and 30 µg/ml α-chymotrypsin (Sigma Chemical Co., St. Louis, Mo., U.S.A., Cat. No. C7762). The pellet was vortexed three times for 2 seconds and the tubes were incubated at room temperature for 20 minutes. The remainder of the procedure is identical to that described in Example 2.

FIG. 4 shows the correlation of log RLU to log CFU/ml for the 65 raw milk samples using this procedure. It indicates a positive correlation between the two methods.

EXAMPLE 4

This example discloses the separation of microbial cells from 88 raw milk samples using a modification of the procedure presented in Example 3.

Figure 5:
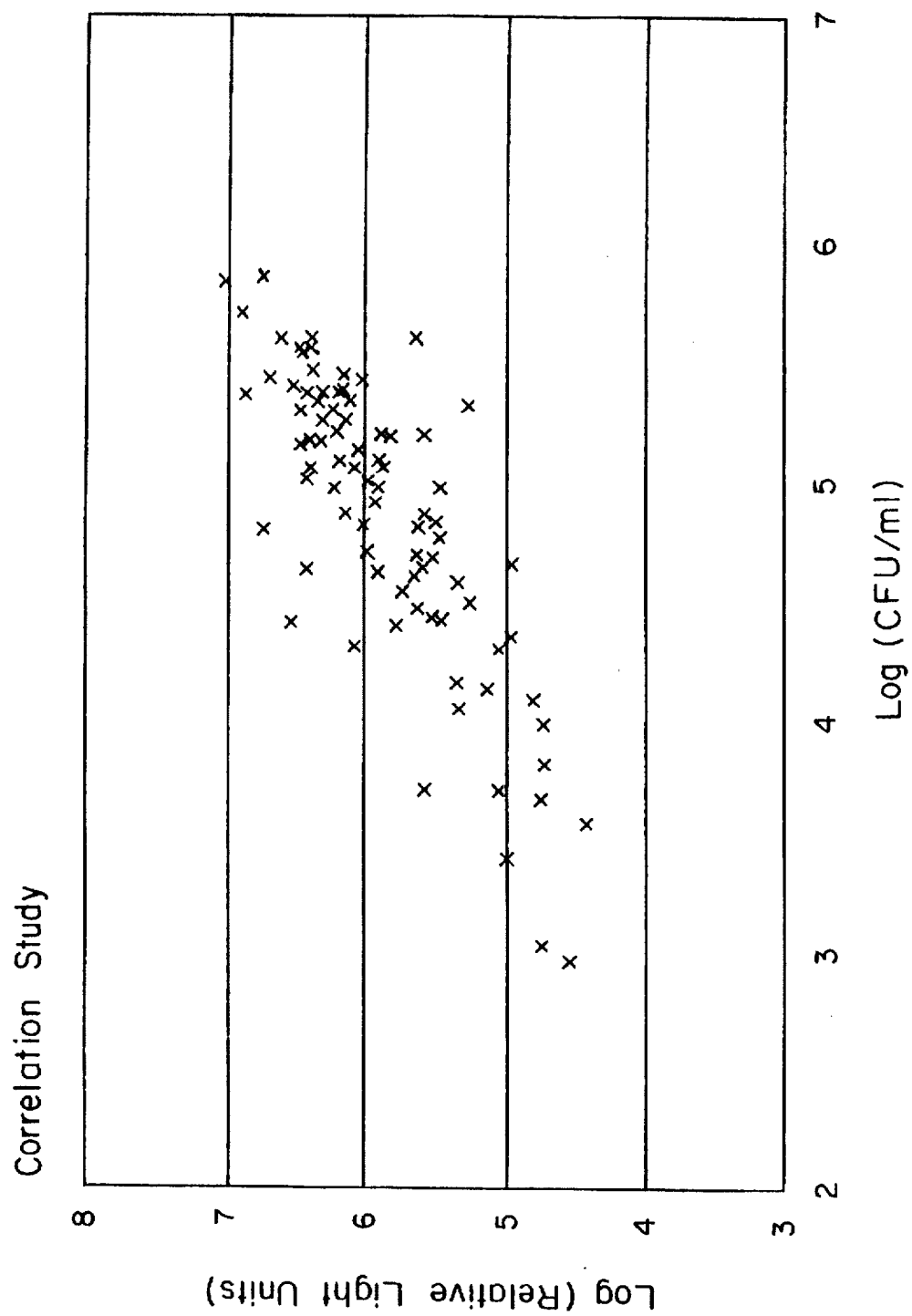
FIG. 5 is a graph showing the correlation between CFU and RLU for the separation of microbial cells from milk described in Example 4.

To 1.0 ml of each raw milk sample was added 500 μl of a solution of 3% nitrilotriacetic acid (sodium salt), 0.5% Triton X-100, and the samples were then treated as in Example 3. After aspirating the supernatants from the first centrifugation step, a solution of 0.05 mM $MgCl_2$, 0.2% Triton X-100 containing 0.01% surfactant-free polystyrene beads (0.984 μm, Bangs Labs, Carmel, Indiana, U.S.A.) and 60 μg/ml α-chymotrypsin. The polystyrene beads centrifuge down with the cells. The samples were incubated, centrifuged, and aspirated as in Example 3, and the pellets were resuspended in 0.05 mM $MgCl_2$, 0.2% Triton X-100, vortexed, and recentrifuged. The remainder of the procedure was performed as described in Example 3. The results of this experiment are shown in FIG. 5. A positive correlation between the two methods was obtained in this study.

EXAMPLE 5

This example discloses the separation of microbial cells from 18 raw milk samples using a modification of the procedure described in Example 4.

In this study an equivalent amount of carrier polystyrene beads (described in Example 4) were added to the 3% nitrilotriacetic acid (sodium salt), 0.5% Triton X-100 solution for the first milk treatment step. Carrier was not added in any subsequent steps. In addition, α-chymotrypsin was used at a final concentration of 150 μg/ml in the first wash solution. The remainder of the procedure is as described in Example 4.

The results of this correlation study are shown in FIG. 6, which shows a correlation between the two procedures.

EXAMPLE 6

This example demonstrates the usefulness of the present invention using a filtration device in the procedure.

A set of inoculated pasteurized milk samples was prepared as in Example 1. Samples corresponding to tubes 1 through 11 in Table 1 (Example 1) were used.

To each sample was added 300 μl of 0.5M EDTA, pH 8.0, and 300 μl of 1% NP-40. The tubes were capped, inverted 10 times to mix, and centrifuged at 12,000×g for 10 minutes. The supernatants were removed by aspiration and the pellets resuspended in 200 μl of 0.1M $MgCl_2$, 0.2% NP-40 and vortexed to resuspend the pellets. These cell suspensions were put into a spin filter device (Millipore, Ultrafree MC, 0.45 μm) and centrifuged at 12,000×g for 10 minutes. After centrifugation the filter insert was removed to a capless sterile microcentrifuge tube, and 50 μl of 1% TCA was added to the filter and allowed to incubate for 10 minutes at room temperature. The filters and holders were re-centrifuged for 10 minutes and the TCA extracts were collected and analyzed as in Example 1.

The results of this experiment are shown in FIG. 7 and demonstrate the usefulness of the present invention in a filtration-type format. A good dose response of RLU is shown over the cell concentration range studied in this example.

EXAMPLE 7

Salmonella typhimurium strain PB637, obtained from a hospital in New England, was grown overnight in a rich broth. The overnight culture was diluted to an $OD_{600}$ of 0.1 and then grown to an $OD_{600}$ of 0.9. The culture was serially ten-fold diluted in phosphate-buffered saline (PBS). An aliquot of each dilution was plated to determine the titer of viable bacteria. Five μl of each dilution was added to 0.995 ml of raw milk in microcentrifuge tubes. There were 7 dilutions plus one blank of PBS with no bacteria. Next 500 μl of the clearing solution (0.25M EDTA, 0.5% Triton X-100, 0.01% microparticulate carrier (surfactant-free polystyrene beads, see Example 4)) was added to each tube. The tubes were inverted ten times to mix thoroughly. The tubes were centrifuged for 5 minutes in a microcentrifuge. The cream layer was removed and the supernatant was aspirated. The cells of the pellet were then washed by resuspending the pellet in 1 ml of PBS with the use of a vortex mixer, followed by adding 500 μl of the resulting cell suspension to a microcentrifuge tube and centrifuging for 5 minutes. The supernatant was removed by aspiration and the resulting pellet was resuspended in 25 μl of distilled water.

Amplification of a 324 base-pair segment of the Salmonella genome (in the ompA gene, for sequence see Freudl and Cole, Eur. J. Biochem. 134:497–502 (1983)) was used for detection of the Salmonella present in the raw milk sample. Oligonucleotides designated A86, and B83, were used as the primers. The primers were mixed such that each primer was at a concentration of 50 μM in sterile, distilled water.

A PCR reagent mix was made by mixing 180 μl of 10×Taq DNA Polymerase Buffer (500 mM KCl, 100 mM Tris-HCl (pH 8.8 at 25° C.), 15 mM $MgCl_2$, 1% Triton X-100) (Promega Corp., Madison, Wis., U.S.A.), 10.8 μl (45 units) of Taq DNA Polymerase (Promega Corp.), 180 μl of dNTP solution (2 mM of each of dATP, dGTP, dCTP and TTP) to provide an initial concentration of 200 μM of each of the dNTP's in the PCR reaction, plus distilled water to a final volume of 1.8 ml. To a new microfuge tube was added 93 μl of the PCR reagent mix and 2 μl of the primer mix (100 pmoles of each primer). Next 5 μl of each bacterial suspension was added to the tube and the liquid was overlaid with 2 drops of mineral oil. The tubes were placed in a Perkin-Elmer Cetus DNA Thermal Cycler (Perkin-Elmer Cetus, Norwalk, Conn., U.S.A.). There were no steps taken to lyse the bacteria or extract the DNA. This was accomplished during the PCR reactions. The Thermal Cycler conditions were set for 1 min at 94° C., then 1 min at 65° C., and finally 2.5 minutes at 72° C. with 5 second autoextend. A total of 35 cycles of PCR were performed.

The PCR products were analyzed by agarose gel electrophoresis. A 1.5% agarose gel in TAE buffer was loaded with 5 μl of each PCR reaction product. The gel was electrophoresed for 1.5 hr at 70 V. The gel was stained with ethidium bromide. The lane from the milk sample with 250 cells/ml of raw milk showed a visible band of the expected fragment length. Dilutions with fewer cells and the PBS control tube (PBS with no cells added to milk) showed no bands on the gel.

The gel was denatured in 0.5M NaOH for 30 minutes at room temperature. It was then washed two times in 1M Tris-HCl for 15 minutes each wash. The gel was then blotted by overlaying the gel with a nylon membrane followed by 0.5 inches of Whatman 3 MM paper and Saran wrap, weighted with two large books. After 2 hours, the nylon was washed for 10 minutes in 2×SSC and UV crosslinked in a UV-Stratalinker 1800 (Stratagene, La Jolla, Calif., U.S.A.) in automatic mode. The gel was hybridized with a $^{32}$P kinase-labelled, 24-base DNA, designated P47, overnight at 62° C. in 2× SSC, 20 mM sodium phosphate, 0.1% SDS, 10×Denhardt's solution, 10% dextran sulfate, and 0.1 mg/ml herring sperm DNA. The nylon was washed 2 times for 15 minutes each at 62° C. in 2×SSC with 0.1% SDS. The nylon was exposed to Kodak XAR film at −70° C. for 5.5 hours. Probe P47 is Salmonella-specific and has the sequence of a segment of the Salmonella ompA gene between the segments with the sequences of the two primers used in the amplification. All of the dilutions of bacteria into raw milk produced a PCR product band that hybridized with P47 while the PBS control did not. The highest dilution had approximately 2.5 viable cells added to the 1 ml of raw milk. Only 1/10th of this material was added to the PCR reaction, indicating that either the sample taken for the PCR reaction just happened to contain one cell or that the culture had some non-viable cells present. In either case, it is clear that the procedure is highly sensitive for detecting Salmonella cells in raw milk.

EXAMPLE 8

An experiment was done to detect Salmonella typhimurium in beef steak. Five samples (25 g) of beef steak were each added to 225 ml tetrathionate broth and stomached in a Stomacher Lab-Blender 400 (Tekmar Co., Cincinnati, Ohio, U.S.A.) with 0, 0.02, 2, 200, and 20,000 Salmonella cells/ml as determined by an initial standard plate count (SPC) of the inoculum done on bismuth sulfite agar plates. The samples were incubated at 37° C. with shaking (150 rpms). At 0, 3 and 24 hours, a plate count and "clearing wash PCR assay" (an assay similar to that described in Example 7, beginning with the clear wash procedure to obtain the initial cell pellet) were performed on each of the five broths. The plate counts were also done on bismuth sulfite agar (selective for and indicative of the growth of the Salmonellae), since it was anticipated that the meat was precontaminated with bacterial flora. Table 8 provides results from the counts on bismuth sulfite agar.

TABLE 8

| | Bismuth Sulfite Plate Counts in Cells/ml # Salmonella Added per Milliliter | | | | |
|---|---|---|---|---|---|
| | 0 | 0.02 | 2 | 200 | 20,000 |
| T = 0 h | 0 | 0 | 1.2 × 10² | 7.0 × 10² | 3.5 × 10⁴ |
| T = 3 h | 0 | 0 | 1.0 × 10² | 4.5 × 10³ | 3.6 × 10⁵ |
| T - 24 h | 9.5 × 10⁶ | 1.2 × 10⁹ | 1.6 × 10⁹ | 1.8 × 10⁹ | 1.6 × 10⁹ |

The clearing solution was as in Example 7 (0.25M EDTA pH 8.0/0.5% Triton X-100/0.01% carrier). The pellets were resuspended in 100 µl PBS and then quickly frozen at −70° C. After all the samples had been taken and prepared, they were thawed and vortexed. 5 µl were withdrawn from each and added to 95 µl of PCR reaction mix (see Example 7). PCR amplification was carried out using the Perkin-Elmer Cetus DNA Thermal Cycler with oligonucleotides designated C84 and A86 as primers. The primers bracket a 284 base-pair segment of the Salmonella ompA gene; this 284-base-pair segment includes a subsegment with the sequence of probe P47. The PCR cycle consisted of 1 min at 95°, 1 min at 65°, and 2 min 30 sec at 72° with a 5 sec autoextend. A 1.5% agarose gel was run on the PCR products. The gel was then treated with NaOH, neutralized, and squash-blotted onto a nylon membrane. The membrane was rinsed and UV crosslinked before being probed with $^{32}$P kinase-labelled P47 as probe. Subsequent autoradiography confirmed that the products were amplified Salmonella genomic DNA segments which included a subsegment with the sequence of P47. A positive signal was noted for the 20,000 cells per ml samples at 0 and 3 hours incubation and at all inoculation concentrations at 24 hours incubation time. Thus, the clearing wash method to concentrate cells following an overnight culture prepared from meat samples is a satisfactory method of sample preparation for PCR analysis for microorganism contamination.

EXAMPLE 9

An experiment was performed to demonstrate the significant improvement in ATP recovery from microbial cells recovered from raw milk samples using a modification of the procedure described in Example 5.

Figure 8:
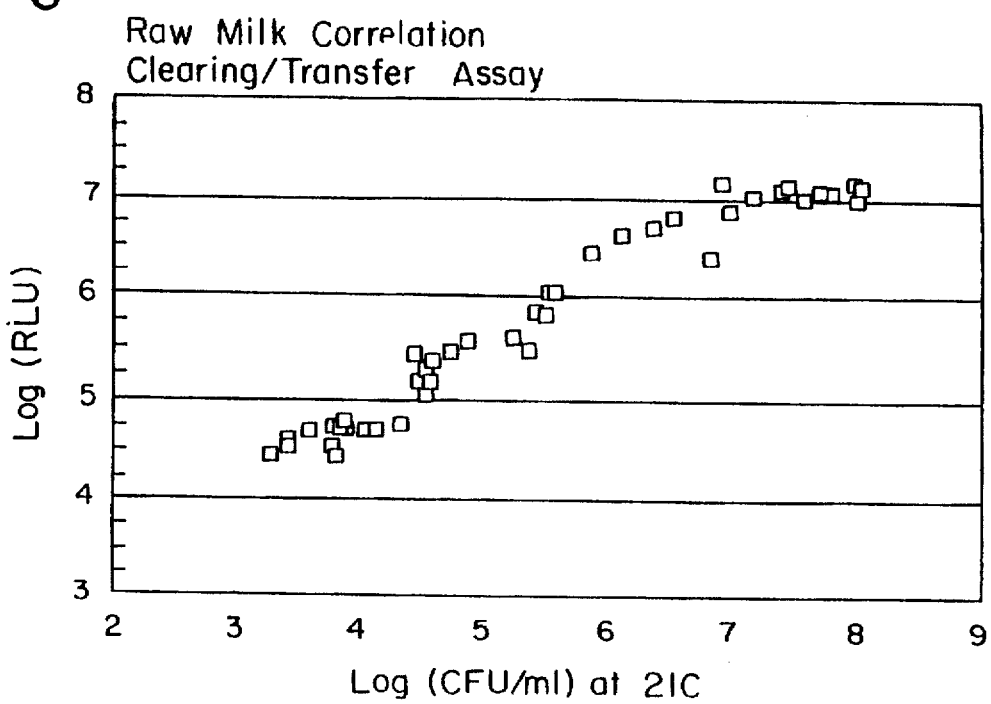
FIG. 8 is a graph showing the correlation between CFU and RLU in the separation of microbial cells from milk as described in Example 9.

In this study cells were isolated as in Example 5 and 0.05 ml of a solution containing 50 µg/ml α-chymotrypsin and 0.001 U/ml potato apyrase (Sigma Chemical, St. Louis, Mo., U.S.A., Grade VI) was added to the microbial pellet. The pellet was mixed with the solution, incubated for approximately 5 minutes at room temperature, and transferred to a luminometer cuvette. A solution containing 0.075% (v/v) chlorhexidine digluconate and 0.00075M Trilon (0.10 ml) was added to the pellet suspension and 0.1 ml of a luciferase/luciferin solution was added to the cuvette. Light output was measured over a 10 second interval and reported as RLU. The results of this procedure are shown in FIG. 8 which shows a correlation between this procedure and standard plate counting.

EXAMPLE 10

An experiment was performed to demonstrate the significant improvement of nitrilotriacetic acid (Trilon) over EDTA in an ATP-based bioluminescent estimation of milk microbiological load. A milk isolated organism (Serratia liquefaciens) was inoculated into Luria broth and shaken overnight at 37°. Cells from the overnight culture were spiked into a pasteurized milk sample to give a final bacterial concentration of 4.7×10⁷ colony forming units per ml of milk. This milk sample was further diluted with pasteurized milk to cover a bacteria range from 4.7×10⁷ cfu/ml to 9.5×10³ cfu/ml. One ml aliquots of each milk sample were mixed with 0.5 ml of one of three types of chelating agent solutions. The first type of solution (chelator 1) was 0.13M nitrilotriacetic acid pH 6.8, 0.5% Triton X-100, and 0.01% microparticle carrier (0.787 micron diameter); the second type of solution (chelator 2) was 0.25M EDTA pH 8, 0.5% Triton X-100, 0.01% microparticle carrier (0.787 micron), and the third type of solution (chelator 3) was 0.25M EDTA pH 12.0, 0.5% Triton X-100, 0.01% microparticle carrier (0.787 micron). Milk samples containing chelating solutions were capped, mixed by inversion and centrifuged for 5 minutes at 12000×g. Supernatants were aspirated from the bacterial microparticle carrier pellets and 100 microliters of a solution containing 0.2% Triton X-100, 0.05 mM magnesium chloride, 0.5% penicillin/streptomycin, 0.05 units/ml of potato apyrase (an ATPase) (Sigma, Grade VI) and 50 µg/ml α-chymotrypsin was added to each pellet. The pellet was resuspended and the entire contents of the microcentrifuge tube was transferred to a luminometer cuvette. The cuvette was placed into a Model 953 Berthold luminometer and 100 microliters of a solution containing 0.075% chlorhexidine digluconate, 0.015% CTAB (Cetyltrimethylammonium bromide) and 0.0015M Trilon.

After a one second delay, 100 microliters of a luciferase-luciferin ("L/L") solution was added and light output was measured over a ten second integration time. Results from this experiment are shown in FIG. 9. Each curve represents a dilution series of milk samples containing variable amounts of Serratia liquifaciens. The first curve in the open squares is a Trilon chelating curve and demonstrates a very nice dose response over three orders of magnitude of cfu/ml. The second and third curves that demonstrate the chelating and background reduction ability of EDTA are also shown in the open triangles and open diamonds. Both curves demonstrate adequate dose response at cfu levels greater that $1 \times 10^5$ although there is a reduction in the RLU recovery from samples that have been chelator treated with EDTA at pH 12. The significant point in this figure is the background that remains at cell titers less than $1 \times 10^5$. Both of the EDTA curves fail to detect cells at an RLU level less than $1 \times 10^5$. This effectively would reduce the potential sensitivity of an assay to about $5 \times 10^5$ colony forming units if an EDTA type solution were used. Utilizing a Trilon based chelating solution however, allows an investigator to detect 10-fold less cells, down to $10^4$ cfu/ml, thus giving a better assay system.

EXAMPLE 11

It was found that N-(2-acetamido) iminodiacetic acid (ADA) is equivalent to nitrilotriacetic acid as a chelator in analyses based on determinations of ATP by bioluminescence. A raw milk sample was serially diluted with a pasteurized milk sample to yield a series of samples with various amounts of raw milk present. The samples were divided into two sets and one set was chelator treated with a solution containing 0.13M nitrilotriacetic acid, 0.5% Triton X-100, and 0.01% microparticle carrier, as in Example 10. The second set of milk samples were treated with a solution containing 0.25M (N-(2-acetamido) iminodiacetic acid) (ADA), 0.5% Triton X-100, 0.01% microparticle carrier, also as in Example 10. Both sets of spiked milk samples were then assayed as described in Example 10. The results of the experiment showed that ADA is an equivalent chelating agent to nitrilotriacetic acid for this type of application.

It is understood that the invention is not limited to the particular embodiments described herein, but embraces such modified forms thereof as come within the scope of the following claims.

We claim:

1. A method of separating and concentrating cells from a liquid milk sample comprising the steps of:

(a) mixing a chelating agent and a microparticulate carrier wherein the microparticulate carrier sediments slightly slower than microbial cells, and wherein the microparticulate carrier serves as a visual indicator facilitating the removal of supernatant without disturbing the cell pellet in the milk sample, (b) centrifuging the sample to form a cell pellet.

2. The method of claim 1 wherein the microparticulate carrier is polystyrene beads with a diameter from about 0.5 µm to about 1.5 µm.

3. The method of any one of claims 1 or 2 wherein the chelating agent is selected from the group consisting of nitrilotriacetic acid and N-(2-acetamido)iminodiacetic acid.

4. The method of any one of claims 1 or 2 including the additional step of removing the supernatant from the cell pellet by aspirating the fluid above the pellet.

5. The method of claim 4 including the additional step of resuspending the pellet in a liquid and testing the suspension to determine the concentration of microbial cells therein by determining ATP in the microbial cells using bioluminescence.

6. The method of claim 4 including the additional step of resuspending the centrifuged pellet in a solution comprising a protease or a protease together with an ATPase.

7. The method of claim 4 including the additional step of suspending the cell pellet in a liquid comprising a lysing agent which lyses somatic cells but not microbial cells.

8. The method of claim 7 wherein said liquid comprising a lysing agent further comprises a protease or a protease together with an ATPase.

9. The method of claim 8 including the additional step of centrifuging the sample after mixing the lysing agent therein, removing the supernatant, resuspending the remaining cell pellet in a liquid, adding an agent to the cell pellet which extracts ATP from microbial cells and quantitatively testing the sample for ATP.

10. The method of claim 8 including the additional step of adding an agent to the cell pellet which extracts ATP from microbial cells and quantitatively testing the sample for ATP.

11. The method of claim 9 wherein the step of testing for ATP includes the steps of adding a luciferase-luciferin reagent to the sample and measuring the relative amount of light emitted from the sample.

12. The method of claim 9 wherein the agent which extracts ATP is a lysing agent which lyses microbial cells.

13. The method of claim 7 including the additional step of centrifuging the suspension, and separating the supernatant from the cells in the pellet which will be primarily microbial cells.

14. The method of claim 13 including the additional step of testing the supernatant liquid separated from the pellet for the concentration of ATP.

15. The method of claim 14 wherein the step of testing for ATP includes the steps of adding a luciferase-luciferin reagent to the supernatant and measuring the relative light emitted from the sample.

16. The method of claim 13 including the additional step of adding an agent to the cells in the pellet which extracts ATP from microbial cells and then testing for the quantitative level of ATP.

17. The method of claim 16 wherein the agent which extracts ATP is a lysing agent.

18. The method of claim 16 wherein the step of testing for the level of ATP comprises adding luciferase-luciferin reagent to the sample and measuring the relative light emitted from the sample.

19. The method of any one of claims 1 or 2 including, before the step of centrifuging, the additional step of mixing a lysing agent with the sample which will lyse somatic cells in the sample but not microbial cells.

20. The method of claim 19 wherein the lysing agent is a non-ionic detergent.

21. The method of claim 19 including the additional steps of removing the supernatant from the pellet, adding a lysing agent to the cell pellet to lyse the cells and testing the lysed sample to determine the relative amount of ATP which is present in the sample.

22. The method of claim 21 wherein the step of testing the lysed samples includes the step of adding a luciferase-luciferin reagent to the sample and measuring the relative light output emitted from the sample.

23. The method of claim 19 including the additional steps of removing the supernatant from the pellet, mixing the cells in the pellet with a liquid comprising a lysing agent which lyses somatic cells but not microbial cells, centrifuging the sample, removing the supernatant liquid, again adding a liquid comprising a lysing agent to the cells in the resulting pellet which lyses somatic cells but not microbial cells, centrifuging the sample, and removing the supernatant, and then testing the resulting pellet for the relative concentration of microbial cells.

24. The method of claim 23 wherein at least the second of said liquids comprising a lysing agent further comprises a protease or a protease together with an ATPase.

25. The method of claim 24 including the additional step of resuspending the centrifuged pellet in a solution that stabilizes the bacterial cells and prevents the loss of cellular metabolites.

26. The method of claim 25 wherein the stabilizing solution contains magnesium ions.

27. The method of claim 26 wherein the stabilizing solution also comprises a protease or a protease together with an ATPase.

28. A microbial test kit for use in testing milk samples, comprising:

(a) a clearing solution comprising a chelating agent, a microparticulate carrier wherein the microparticulate carrier sediments slightly slower than microbial cells, and wherein the microparticulate carrier serves as a visual indicator facilitating the removal of supernatant without disturbing the cell pellet in the milk sample and a somatic cell lysing agent;

(b) a solution comprising an ATP extractant which releases microbial cell ATP; and (c) an ATP detection reagent.

29. The test kit of claim 28 wherein said microparticulate carrier is polystyrene beads with a diameter from about 0.5 µm to about 1.5 µm.

30. The test kit of any one of claims 28 or 29 including (1) a solution for washing a cell pellet resulting from centrifugation, (2) a buffer solution, and a solution for treating the cells in the pellet, said treatment solution comprising a protease or a protease together with an ATPase.

31. The test kit of any one of claims 28 or 29 wherein the ATP detection reagent is luciferin-luciferase, the ATP extractant is a lysing agent which lyses microbial cells, and the somatic cell lysing agent is a non-ionic detergent.

32. The test kit of any one of claims 28 or 29 wherein the chelating agent is selected from the group consisting of nitrilotriacetic acid and N-(2-acetamido)iminodiacetic acid.

33. The test kit of any one of claims 28 or 29 further including a filter for filtering cells from milk components.

34. The test kit of any one of claims 28 or 29 wherein the ATP extractant is selected from the group consisting of trichloroacetic acid, chlorhexidine, and CTAB.

35. The test kit of claim 34 wherein the chelating agent is selected from the group consisting of nitrilotriacetic acid and N-(2-acetamido)iminodiacetic acid.

36. A test kit for use in testing milk samples for somatic cells, comprising:

(a) a clearing solution comprising a chelating agent and microparticulate carrier wherein the microparticulate carrier sediments slightly slower than microbial cells, and wherein the microparticulate carrier serves as a visual indicator facilitating the removal of supernatant without disturbing the cell pellet in the milk sample;

(b) a solution comprising an agent which lyses somatic cells but not microbial cells; and (c) an ATP detection reagent.

37. A test kit according to claim 36 wherein the microparticulate carrier is polystyrene beads with a diameter from about 0.5 µm to about 1.5 µm.

38. The test kit of any one of claims 36 or 37 wherein the ATP detection reagent is luciferin-luciferase.

39. The test kit of any one of claims 36 or 37 wherein the somatic cell lysing agent is a non-ionic detergent.

40. The test kit of any one of claims 36 or 37 wherein the chelating agent is selected from the group consisting of nitrilotriacetic acid and N-(2-acetamido)iminodiacetic acid.

41. The test kit of any one of claims 36 or 37 further including a filter for filtering cells from milk components.

42. A method of treating a liquid milk sample whereby cells in the sample are separated from other milk components and concentrated, comprising the steps of:

(a) mixing a chelating agent and a microparticulate carrier wherein the macroparticulate carrier sediments slightly slower than microbial cells, and wherein the microparticulate carrier serves as a visual indicator facilitating the removal of supernatant without disturbing the cell pellet with the milk sample;

(b) separating the cells in the sample from milk components.

43. A method according to claim 42 wherein the microparticulate carrier is polystyrene beads with a diameter from about 0.5 µm to about 1.5 µm.

44. The method of any one of claims 42 or 43 wherein the step of separating the cells includes the step of filtering the sample with a filter which blocks cells and passes other milk components bound by the chelating agent.

45. The method of any one of claims 42 or 43 wherein the chelating agent is selected from the group consisting of nitrilotriacetic acid and N-(2-acetamido)iminodiacetic acid.

46. The method of any one of claims 42 or 43 wherein the step of separating is carried out by centrifuging the sample to form a cell pellet.

47. The method of claim 46 including the additional step of removing the supernatant from the cell pellet.

48. A clearing solution for use in testing milk samples, comprising a chelating agent, a microparticulate carrier wherein the microparticulate carrier sediments slightly slower than microbial cells, and wherein the microparticulate carrier serves as a visual indicator facilitating the removal of supernatant without disturbing the cell pellet in the milk sample and a somatic cell lysing agent.

49. A clearing solution according to claim 48 wherein the microparticulate carrier is polystyrene beads with a diameter from about 0.5 µm to about 1.5 µm.

50. A clearing solution according to any one of claims 48 or 49 wherein the somatic cell lysing agent is a non-ionic detergent.

51. A clearing solution according to any one of claims 48 or 49 wherein the chelating agent is selected from the group consisting of nitrilotriacetic acid and N-(2-acetamido) iminodiacetic acid.

52. A clearing solution comprising an aliquot of a culture or extract of a material of biological origin, said solution combined with a microparticulate carrier wherein the microparticulate carrier sediments slightly slower than microbial cells, and wherein the microparticulate carrier serves as a visual indicator facilitating the removal of supernatant without disturbing the cell pellet of the culture or the extract, wherein said microparticulate carrier is in suspension in the solution.

53. A solution of claim 52 wherein the microparticulate carrier is polystyrene beads with a diameter from about 0.5 µm to about 1.5 µm.

54. A solution of claim 52 wherein the material of biological origin is a food material other than milk or a milk product.

55. A solution of claim 54 wherein the material of biological origin is a meat and the clearing solution comprises an aliquot of a culture prepared from the meat.

56. A method of separating and concentrating cells from an aliquot of a culture or extract of a material of biological origin comprising the steps of:
(a) combining said aliquot with an aqueous suspension of a microparticulate carrier to form a clearing solution;
(b) centrifuging the clearing solution to form a cell pellet wherein the microparticulate carrier sediments slightly slower than microbial cells, and wherein the microparticulate carrier serves as a visual indicator facilitating the removal of supernatant without disturbing the cell pellet in the culture or extract.

57. The method of claim 56 wherein the microparticulate carrier is polystyrene beads with a diameter from about 0.5 µm to about 1.5 µm.

58. The method of claim 56 wherein the material of biological origin is a food material other than milk or a milk product.

59. The method of claim 58 wherein the material of biological origin is a meat.

* * * * *

UNITED STATES PATENT AND TRADEMARK OFFICE
CERTIFICATE OF CORRECTION

PATENT NO. : 5,700,645  Page 1 of 2

DATED : December 23, 1997

INVENTOR(S) : Edward E. Pahuski; Randall L. Dimond; John H. Priest; Lisa Zandt; Kathleen K. Stebnitz; Leopoldo G. Mendoza It is certified that error appears in the above-identified patent and that said Letters Patent is hereby corrected as shown below:

Column 15, line 3 delete "gown" and insert in its place

--grown--.

Column 15, line 48 delete "piper" and insert in its place

--pipet--.

UNITED STATES PATENT AND TRADEMARK OFFICE
CERTIFICATE OF CORRECTION

PATENT NO. : 5,700,645
DATED : December 23, 1997
INVENTOR(S) : Edward E. Pahuski; Randall L. Dimond; John H. Priest; Lisa Zandt; Kathleen K. Stebnitz; Leopoldo G. Mendoza It is certified that error appears in the above-identified patent and that said Letters Patent is hereby corrected as shown below:

Column 15, line 63 delete "piper" and insert in its place --pipet--.

Column 16, line 44 delete "piperted" and insert in its place --pipetted--.

Column 16, line 47 delete "." following the word "The".

Signed and Sealed this

Eleventh Day of May, 1999

Attest:

Q. TODD DICKINSON

*Attesting Officer*  *Acting Commissioner of Patents and Trademarks*